United States Patent
Provins et al.

(10) Patent No.: US 11,155,565 B2
(45) Date of Patent: Oct. 26, 2021

(54) 2-OXO-1,3-OXAZOLIDINYL IMIDAZOTHIADIAZOLE DERIVATIVES

(71) Applicant: UCB Biopharma SRL, Brussels (BE)

(72) Inventors: Laurent Provins, Brussels (BE); Hugues Chanteux, Brussels (BE); Yannick Quesnel, Brussels (BE)

(73) Assignee: UCB Biopharma SRL

( * ) Notice: Subject to any disclaimer, the term of this patent is extended or adjusted under 35 U.S.C. 154(b) by 0 days.

(21) Appl. No.: 16/629,776

(22) PCT Filed: Jul. 5, 2018

(86) PCT No.: PCT/EP2018/068207
§ 371 (c)(1),
(2) Date: Jan. 9, 2020

(87) PCT Pub. No.: WO2019/011770
PCT Pub. Date: Jan. 17, 2019

(65) Prior Publication Data
US 2020/0231599 A1    Jul. 23, 2020

(30) Foreign Application Priority Data
Jul. 10, 2017 (EP) .................... 17180432

(51) Int. Cl.
*C07D 513/04*    (2006.01)
*A61P 25/08*    (2006.01)

(52) U.S. Cl.
CPC ............ *C07D 513/04* (2013.01); *A61P 25/08* (2018.01)

(58) Field of Classification Search
CPC .................................................... C07D 513/04
USPC .......................................................... 514/363
See application file for complete search history.

(56) References Cited

FOREIGN PATENT DOCUMENTS

| WO | WO2008/132139 | 11/2008 |
| WO | WO2011/047860 | 4/2011 |
| WO | WO2012/143116 | 10/2012 |
| WO | WO2012/143117 | 10/2012 |

*Primary Examiner* — Kahsay Habte
(74) *Attorney, Agent, or Firm* — McDonnell Boehnen Hulbert & Berghoff LLP

(57) ABSTRACT

The present invention relates to 2-oxo-1,3-oxazolidinyl imidazothiadiazole derivatives, processes for preparing them, pharmaceutical compositions containing them and their use as pharmaceuticals.

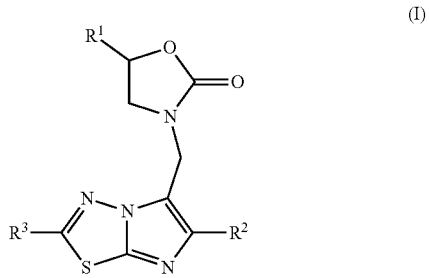

(I)

15 Claims, No Drawings

2-OXO-1,3-OXAZOLIDINYL IMIDAZOTHIADIAZOLE DERIVATIVES

CROSS-REFERENCE TO RELATED APPLICATIONS

This application is a U.S. national phase of International Application No. PCT/EP2018/068207, filed Jul. 5, 2018, which claims priority from European Patent Application EP17180432.1, filed Jul. 10, 2017, the disclosure of each of which is hereby incorporated by reference in its entirety.

INTRODUCTION

The present invention relates to 2-oxo-1,3-oxazolidinyl imidazothiadiazole derivatives, processes for preparing them, pharmaceutical compositions containing them and their use as pharmaceuticals.

A persistent problem in seizure control arises with those patients who do not at all or only insufficiently respond to currently available treatments. Those patients are viewed as being refractory to treatment and represent a considerable challenge for the medical community. It is estimated that about 30% of epilepsy patients are to be classified as being refractory. Hence, there is a need to develop new medications that specifically target this population of patients.

Anti-epileptic compounds of formula (A) are disclosed in WO 2008/132139:

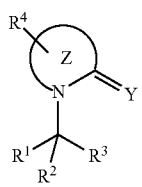

(A)

wherein
Y is O or S;
$R^1$ is hydrogen or $C_{1-6}$ alkyl;
$R^2$ is hydrogen;
$R^3$ is —$CONR^5R^6$, —$COR^7$, an imidazolyl, an imidazopyridinyl, an imidazopyridazinyl;
$R^5$, $R^6$ are the same or different and are independently selected from hydrogen and $C_{1-6}$ alkyl;
$R^7$ is $C_{1-6}$ alkyl;
Z is a monocyclic or bicyclic heterocyclic moiety selected from the group consisting of imidazolidin-1-yl, 1,3-oxazolidin-3-yl, 2,5-dihydro-1H-pyrrol-1-yl, 1,3-thiazol-3(2H)-yl, 1,3-thiazolidin-3-yl, piperidin-1-yl, azepan-1-yl, 5,6-dihydro-4H-thieno[3,2-b]pyrrol-4-yl, hexahydro-4H-thieno[3,2-b]pyrrol-4-yl, 2,3-dihydro-1H-thieno[3,4-b]pyrrol-1-yl, 1,3-benzothiazol-3(2H)-yl, 1,3-benzoxazol-3(2H)-yl, pyrazolo[1,5-a]pyridin-1(2H)-yl, 3,4-dihydroisoquinolin-2(1H)-yl, 3,4-dihydroquinolin-1(2H)-yl, 1,3,4,5-tetrahydro-2H-2-benzazepin-2-yl, 1,2,4,5-tetrahydro-3H-3-benzazepin-3-yl.

In a specific embodiment of WO 2008/132139 the Z=Y moiety in formula (A) could be:

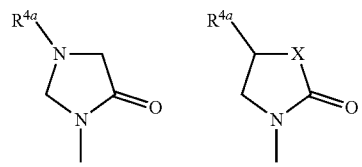

wherein X is O or S.

Anti-epileptic compounds of formula (I) are disclosed in WO 2011/047860: 2-oxo-1-pyrrolidinyl imidazothiadiazole derivatives according to formula (I)

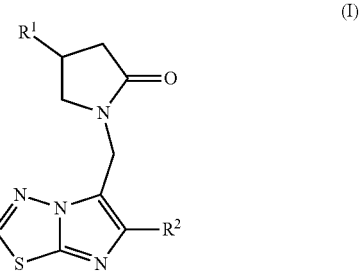

(I)

wherein
$R^1$ is a $C_{1-4}$ alkyl containing at least one halogen substituent;
$R^2$ is either a halogen (chlorine, bromine, iodine) or a $C_{1-4}$ alkyl containing at least one halogen substituent;
$R^3$ is a $C_{1-4}$ alkyl (e.g. a methyl or ethyl) containing at least one hydroxy (OH) or an alkoxy (e.g. methoxy or ethoxy or propoxy) substituent.

Anti-epileptic compounds of formula (I) are disclosed in WO 2012/143116: 4-oxo-1-imidazolidinyl imidazothiadiazole derivatives according to formula (I),

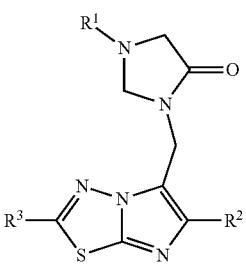

(I)

wherein
$R^1$ is a $C_{1-4}$ alkyl optionally substituted by one or more (1 to 6, preferably 2, 3 or 5) halogens, by a substituted or unsubstituted phenyl or by a substituted or unsubstituted $C_{1-4}$ cycloalkyl;
$R^2$ is either a halogen (chlorine, bromine, iodine) or a $C_{1-4}$ alkyl containing one or more (i.e. 1, 2 or 3) halogen substituents;
$R^3$ is a $C_{1-4}$ alkyl (e.g. a methyl or ethyl) containing at least one hydroxy (OH) or an alkoxy (e.g. methoxy or ethoxy or propoxy) substituent.

The invention provides new 2-oxo-1,3-oxazolidinyl imidazothiadiazole derivatives having the formula (I), their geometrical isomers, enantiomers, diastereoisomers and mixtures, or a pharmaceutically acceptable salt thereof,

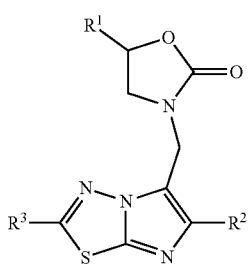

Further aspects of the invention will become apparent from the detailed description.

DETAILED DESCRIPTION OF THE INVENTION

The present invention relates to 2-oxo-1,3-oxazolidinyl imidazothiadiazole derivatives according to formula (I),

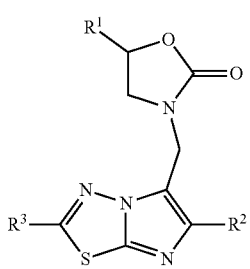

wherein
$R^1$ is a $C_{1-4}$ alkyl optionally substituted by one or more halogen substituents;
$R^2$ is a halogen atom or a $C_{1-4}$ alkyl optionally substituted by one or more halogen atoms;
$R^3$ is a $C_{1-4}$ alkyl substituted by an alkoxy substituent.

Also comprised are tautomers, geometrical isomers, enantiomers, diastereomers, isotopes and mixtures, or a pharmaceutically acceptable salt of compounds of formula (I) as well as any deuterated variant.

In specific embodiment, $R^1$ is an i-butyl, a n-propyl, a 2,2-difluoropropyl, a 2-chloro-2,2-difluoroethyl, a 2,2-difluoroethyl, a 2,2,2-trifluoroethyl or a 2-fluoroethyl moiety.

In a more specific embodiment, $R^1$ is a n-propyl, a 2-chloro-2,2-difluoroethyl, a 2,2-difluoropropyl or a 2,2,2-trifluoroethyl moiety.

Preferably, $R^1$ is a 2,2-difluoropropyl, a 2,2,2-trifluoroethyl or a n-propyl moiety.

In a further specific embodiment, $R^2$ is a chlorine atom, a difluoromethyl moiety, or a trifluoromethyl moiety.

In a preferred embodiment, $R^2$ is a difluoromethyl moiety or a trifluoromethyl moiety.

In a further specific embodiment, $R^3$ is methoxymethyl, a [($^2H_3$)methyloxy]methyl, a methoxy($^2H_2$)methyl, or a [($^2H_3$)methyloxy]($^2H_2$)methyl moiety.

In a preferred embodiment, $R^3$ is a methoxymethyl moiety.

In a further specific embodiment, compounds of formula (I) are those wherein:
$R^1$ is a n-propyl moiety, a 2-chloro-2,2-difluoroethyl, a 2,2-difluoropropyl or a 2,2,2-trifluoroethyl moiety;
$R^2$ is a chlorine atom, a difluoromethyl, or a trifluoromethyl moiety;
$R^3$ is a methoxymethyl, a [($^2H_3$)methyloxy]methyl, a methoxy($^2H_2$)methyl, or a [($^2H_3$)methyloxy]($^2H_2$) methyl moiety.

In a further specific embodiment, compounds of formula (I) are those wherein:
$R^1$ is a n-propyl moiety; a 2,2-difluoropropyl or a 2,2,2-trifluoroethyl moiety
$R^2$ is a difluoromethyl or a trifluoromethyl moiety;
$R^3$ is a methoxymethyl, a [($^2H_3$)methyloxy]methyl, a methoxy($^2H_2$)methyl, or a [($^2H_3$)methyloxy]($^2H_2$) methyl moiety.

In a preferred embodiment, compounds of formula (I) are those wherein:
$R^1$ is a n-propyl moiety; a 2,2-difluoropropyl or a 2,2,2-trifluoroethyl moiety;
$R^2$ is a difluoromethyl or a trifluoromethyl moiety;
$R^3$ is a methoxymethyl moiety.

Specific compounds of the present invention are those selected from the group consisting of:
(+)-3-[[2-(methoxymethyl)-6-(trifluoromethyl)imidazo[2,1-b][1,3,4]thiadiazol-5-yl]methyl]-5-propyl-oxazolidin-2-one;
(−)-3-[[2-(methoxymethyl)-6-(trifluoromethyl)imidazo[2,1-b][1,3,4]thiadiazol-5-yl]methyl]-5-propyl-oxazolidin-2-one;
(+)-3-[[6-(difluoromethyl)-2-(methoxymethyl)imidazo[2,1-b][1,3,4]thiadiazol-5-yl]methyl]-5-propyl-oxazolidin-2-one;
(−)-3-[[6-(difluoromethyl)-2-(methoxymethyl)imidazo[2,1-b][1,3,4]thiadiazol-5-yl]methyl]-5-propyl-oxazolidin-2-one;
(+)-3-[[2-[dideuterio(methoxy)methyl]-6-(trifluoromethyl)imidazo[2,1-b][1,3,4]thiadiazol-5-yl]methyl]-5-propyl-oxazolidin-2-one;
(−)-3-[[2-[dideuterio(methoxy)methyl]-6-(trifluoromethyl)imidazo[2,1-b][1,3,4]thiadiazol-5-yl]methyl]-5-propyl-oxazolidin-2-one;
(+)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one;
(−)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one;
(+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one;
(−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one;
(+)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one;
(−)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one;
(−)-5-(2,2-difluoropropyl)-3-[[2-(methoxymethyl)-6-(trifluoromethyl)imidazo[2,1-b][1,3,4]thiadiazol-5-yl]methyl]oxazolidin-2-one;
(+)-5-(2,2-difluoropropyl)-3-[[2-(methoxymethyl)-6-(trifluoromethyl)imidazo[2,1-b][1,3,4]thiadiazol-5-yl]methyl]oxazolidin-2-one;
3-[[6-(difluoromethyl)-2-(methoxymethyl)imidazo[2,1-b][1,3,4]thiadiazol-5-yl]methyl]-5-(2,2-difluoropropyl)oxazolidin-2-one, enantiomer 1;

3-[[6-(difluoromethyl)-2-(methoxymethyl)imidazo[2,1-b]
[1,3,4]thiadiazol-5-yl]methyl]-5-(2,2-difluoropropyl)
oxazolidin-2-one, enantiomer 2.

The compounds of the present invention are for use as a medicament, in the treatment of epilepsy, epileptogenesis, seizure disorders, convulsions, in particular for refractory seizures.

The following paragraphs provide definitions of the various chemical moieties that make up the compounds according to the invention and are intended to apply uniformly throughout the specification and claims unless an otherwise expressly set out definition provides a broader definition.

"$C_{1-4}$ alkyl" refers to alkyl groups having 1 to 4 carbon atoms. This term is exemplified by groups such as methyl, ethyl, n-propyl, isopropyl, n-butyl, isobutyl, tert-butyl. "$C_{1-4}$ alkyl" groups may be substituted by one or more substituents selected from halogen, or alkoxy.

Any moiety "H" in formula (I) may be the isotope hydrogen, deuterium or tritium.

"Alkoxy" refers to the group —O—R where R includes "$C_{1-4}$ alkyl".

"Halogen" refers to fluoro, chloro, bromo and iodo atoms, preferably fluoro and chloro.

The "pharmaceutically acceptable salts" according to the invention include therapeutically active, non-toxic acid or base salt forms which the compounds of formula (I) are able to form.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula (I) and their salts can be in the form of a solvate, which is included within the scope of the present invention. Such solvates include for example hydrates, alcoholates and the like.

Compounds of formula (I) and/or their intermediates may have at least one stereogenic center in their structure. This stereogenic center may be present in a R or a S configuration, said R and S notation is used in correspondence with the rules described in Pure Appl. Chem., 45 (1976) 11-30. The invention thus also relates to all stereoisomeric forms such as enantiomeric and diastereoisomeric forms of the compounds of formula (I) or mixtures thereof (including all possible mixtures of stereoisomers). With respect to the present invention reference to a compound or compounds is intended to encompass that compound in each of its possible isomeric forms and mixtures thereof, unless the particular isomeric form is referred to specifically. The expression "enantiomerically pure" as used herein refers to compounds which have enantiomeric excess (ee) greater than 95%.

Compounds according to the present invention may exist in different polymorphic forms. Although not explicitly indicated in the above formula, such forms are intended to be included within the scope of the present invention.

The compounds of formula (I) according to the invention can be prepared analogously to conventional methods as understood by the person skilled in the art of synthetic organic chemistry.

According to one embodiment, compounds having the general formula (I) may be prepared by reaction of a compound of formula (II) with an urea of formula (III) according to the equation:

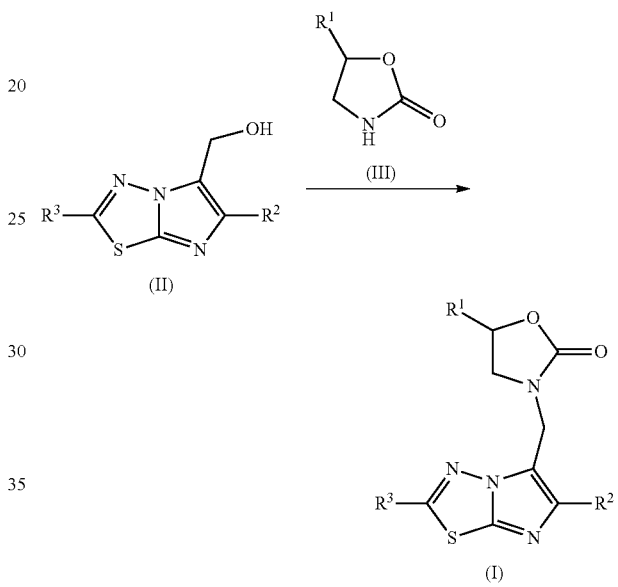

wherein $R^1$, $R^2$ and $R^3$ have the same definitions as defined above for compounds of formula (I).

This reaction may be performed using an acid such as p-toluenesulfonic acid in an aprotic solvent such as sulfolane at high temperature.

Compounds of formula (II) may be prepared by hydroxymethylation of a compound of formula (IV) according to the equation:

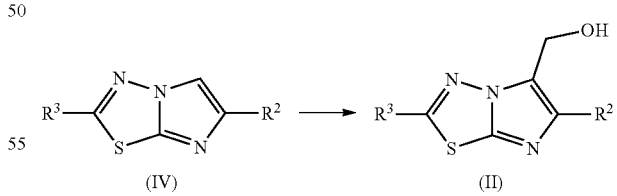

wherein $R^2$ and $R^3$ have the same definition as defined above for compounds of formula (I).

This reaction may be performed using a formylating agent such as paraformaldehyde under acidic conditions in a polar solvent such as dioxane at 100° C., or according to any other method known to the person skilled in the art.

Compounds of formula (IV) may be synthesized by reaction of a compound of formula (V) with a bromo derivative of formula (VI) according to the equation:

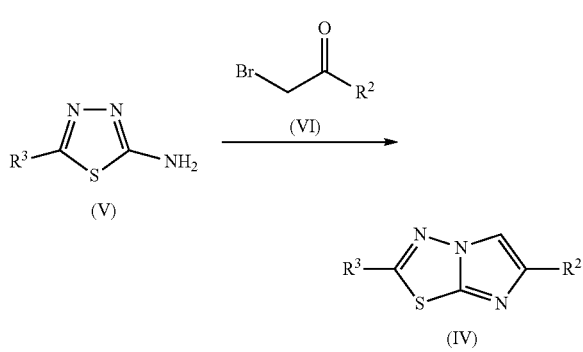

wherein $R^2$ and $R^3$ have the same definition as described above for compounds of formula (I).

This reaction can be performed using procedures described in the literature or known to the person skilled in the art.

Compounds of formula (V) and compounds of formula (VI) are either commercially available or may be synthesized according to any method known to the person skilled in the art.

According to one embodiment, compounds of formula (III) may be prepared by cyclization of a compound of formula (VII) according to the equation:

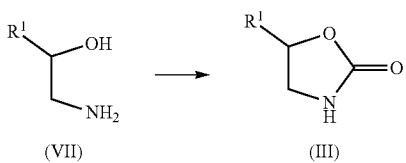

This reaction may be performed with 1,1'-carbonyldiimidazole in a polar solvent such as tetrahydrofuran in the presence of a base such as sodium hydride at room temperature or using procedures known to the person skilled in the art.

Compounds of formula (VII) may be prepared by reduction of a compound of formula (VIII) according to the equation

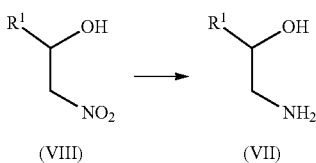

wherein $R^1$ has the same definition as defined above.

This reaction may be performed using a reducing agent such as, but not limited to, hydrogen in the presence of a catalyst such as palladium on charcoal in a polar solvent such as ethanol or by other procedures known to the person skilled in the art.

Compounds of formula (VIII) may be prepared starting from commercially available aldehydes or alcohols wherein $R^1$ has the same definition as defined above according to any reaction sequence known to the person skilled in the art.

The compounds of the present invention are for use as a medicament, in the treatment of epilepsy, epileptogenesis, seizure disorders, convulsions, in particular for refractory seizures.

Seizures can be classified as refractory when a patient fails to achieve seizure freedom for 12 months or more of state of the art treatment with two or more anti-epileptic drugs at maximal tolerated doses. The International League Against Epilepsy (ILAE) has defined drug resistant epilepsy as "failure of adequate trials of two tolerated and appropriately chosen and used AED schedules (whether as monotherapies or in combination) to achieve sustained seizure freedom".

The methods of the invention comprise administration to a mammal (preferably a human) suffering from above mentioned conditions or disorders, of a compound according to the invention in an amount sufficient to alleviate or prevent the disorder or condition.

The compound is conveniently administered in any suitable unit dosage form, including but not limited to one containing 1 to 2000 mg, preferably 1 to 1000 mg, more preferably 1 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manisfestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

A further aspect of the present invention relates to a pharmaceutical composition comprising an effective amount of a compound of formula (I) in combination with a pharmaceutically acceptable diluent or carrier.

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner.

Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

In accordance with the invention it has also been found that the compounds of formula (I) or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenytoin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

For oral compositions, the daily dosage is in the range 1 mg to 2000 mg of compounds of formula (I). Preferably in the range 1 mg to 1000 mg of compounds of formula (I), most preferably 1 mg to 500 mg.

In compositions for parenteral administration, the quantity of compound of formula (I) present is at least 0.5% by weight and can be up to 33% by weight with respect to the total weight of the composition. For the preferred parenteral compositions, the dosage unit is in the range 1 mg to 2000 mg of compounds of formula (I).

The daily dose can fall within a wide range of dosage units of compound of formula (I) and is generally in the range 1 to 2000 mg, preferably 1 to 1000 mg. However, it should be understood that the specific doses can be adapted to particular cases depending on the individual requirements, at the physician's discretion.

The SV2 proteins binding compounds provided by this invention and labeled derivatives thereof may be useful as standards and reagents in determining the ability of tested compounds (e.g., a potential pharmaceutical) to bind to the SV2 proteins.

Labeled derivatives of SV2 proteins' ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A and SV2C, but including SV2B, to a putative agent and incubating the membranes or proteins or fragments and the agent with labelled compound of formula (I). The method further comprises determining if the binding of the compound of formula (I) to the protein is inhibited by the putative agent, thereby identifying binding partners for the protein. Thus, the screening assays enable the identification of new drugs or compounds that interact with SV2 proteins. The present invention also provides photoactivable ligands of SV2 proteins.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3$H, a fluorescent label, an enzyme, europium, biotin and other conventional labels for assays of this type.

Labelled compounds of formula (I) are useful in the methods as probes in assays to screen for new compounds or agents that bind to the SV2 proteins (SV2A, SV2B and SV2C). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly. Possibilities for direct labelling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of anti-ligand antibodies. The compounds may also include spacers or linkers in cases where the compounds are to be attached to a solid support. To identify agents or compounds which compete or interact with labelled ligands according to the invention for binding to the SV2 proteins (especially SV2A and SV2C), intact cells, cellular or membrane fragments containing SV2A or SV2C or the entire SV2 protein or a fragment thereof can be used. The agent or compound may be incubated with the cells, membranes, SV2 protein or fragment prior to, at the same time as, or after incubation with labelled levetiracetam or an analog or derivative thereof. Assays may be modified or prepared in any available format, including high-throughput screening (HTS) assays that monitor the binding of levetiracetam or the binding of derivatives or analogs thereof to SV2 proteins or fragments thereof. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labeled ligand according to the invention to SV2 or a fragment of SV2 or of labelled levetiracetam, or derivatives or analogs thereof, to SV2 or a fragment of SV2 protein. The inhibition of complex formation may be detected by a variety of techniques such as filtration assays, Flashplates (Perkin Elmer), scintillation proximity assays (SPA, GE). For high-throughput screenings (HTS), scintillation proximity assay which uses microspheres coated with biological membranes or flashplates coated with biological membranes are powerful methods that do not require separation or washing steps.

A problem which can be faced when developing compounds for use in therapy is the capacity of certain compounds (perpetrator drugs), which could be co-administered together with the compounds of the present invention (victim drugs), to induce CYP450 enzymes, in particular CYP3A4/5. The induction of such enzymes by the perpetrator drugs may impact the exposure of the victim drug, when mainly metabolized by CYP450 enzymes and CYP3A4/5 in particular, thereby potentially altering their efficacy profile. It is therefore desirable to develop compounds with limited potential for metabolization by CYP3A4/5 enzymes.

The CYP3A4/5 contribution to the total metabolism of compounds according to the present invention has been evaluated by calculating the ratio between human hepatocytes clearances in absence and presence of a selective CYP3A4/5 inhibitor such as azamulin.

When tested in this assay according to the protocol described in the present patent application, compounds according to the present invention exhibit a fraction metabolized by CYP3A4/5 ($F_{m,CYP3A4/5}$) typically lower than 40%, therefore minimizing the risk for drug-drug interactions when coadministered with CYP450 inducers.

EXPERIMENTAL SECTION

Abbreviations/Recurrent Reagents
Ac: acetyl
ACN: Acetonitrile
Brine: Saturated aqueous sodium chloride solution
nBu: n-butyl
tBu: tert-butyl
Bz: benzoyl
CV: column volumes
DCM: Dichloromethane
DMF: N,N-Dimethylformamide
DMSO: Dimethylsulfoxide
Et: Ethyl
EtOH: Ethanol
Et$_2$O: Diethyl ether
EtOAc: Ethyl acetate
h: Hour
HPLC: High Pressure Liquid Chromatography
LC: Liquid Chromatography
LCMS: Liquid Chromatography Mass Spectrometry
MeOH: Methanol
min.: minutes
NMR: Nuclear magnetic resonance
PrOH: isopropanol
PTSA: p-toluenesulfonic acid
RT: room temperature
SFC: Supercritical Fluid Chromatography
THF: Tetrahydrofuran
TLC: Thin Layer Chromatography In the present application, the IUPAC name (or the name generated from Accelerys Draw 4.0) of the compounds is mentioned.

Analytical Methods

All reactions involving air or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4.6 mm column. The gradient runs from 100% solvent A (water/ACN/ammonium formate solution 85/5/10 (v/v/v)) to 100% solvent B (water/ACN/ammonium formate solution 5/85/10 (v/v/v)) in 6 min. with a hold at 100% B of 5 minutes. The flow rate is set at 8 mL/min during 6 min. then increased at 3 mL/min during 2 min. with a hold at 3 mL/min during 3 minutes. A split of 1/25 is used just before API source. The chromatography is carried out at 45°

C. The ammonium formate solution (pH-8.5) is prepared by dissolution of ammonium formate (630 mg) in water (1 L) and addition of ammonium hydroxide 30% (500 µL).

It will be apparent to the one skilled in the art that different retention times may be obtained for LC data if different analytical conditions are used.

Mass spectrometric measurements in LCMS mode are performed as follows:

For basic elution, analyses are performed using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an basic elution. The reverse phase separation is carried out at 45° C. on a Waters Acquity UPLC BEHC18 1.7 µm (2.1×50 mm) column for basic elution. Gradient elution is done with water/ACN/ammonium formate (95/5/63 mg/L) (solvent A) and ACN/water/ammonium formate (95/5/63 mg/L) (solvent B). Injection volume: 1 µL. Full flow in MS.

Basic Program "4 Min"

| Time (min) | A (%) | B (%) | Flow (mL/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

Basic Program "10 Min"

| Time (min) | A (%) | B (%) | Flow (mL/min) |
|---|---|---|---|
| 0 | 99 | 1 | 0.4 |
| 0.8 | 99 | 1 | 0.4 |
| 5.3 | 0 | 100 | 0.4 |
| 5.35 | 0 | 100 | 0.5 |
| 7.30 | 0 | 100 | 0.5 |

For acidic elution, analyses are performed using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an acidic elution. The reverse phase separation is carried out at 45° C. on a Waters Acquity UPLC HSS T3 1.8 µm (2.1×50 mm) column for acidic elution. Gradient elution is done with water/ACN/TFA (95/5/0.5 mL/L) (solvent A) and ACN (solvent B). Injection volume: 1 µL. Full flow in MS.

Acidic Program "4 Min"

| Time (min) | A (%) | B (%) | Flow (mL/min) |
|---|---|---|---|
| 0 | 99 | 1 | 0.4 |
| 0.3 | 99 | 1 | 0.4 |
| 3.2 | 5 | 95 | 0.4 |
| 3.25 | 5 | 95 | 0.5 |
| 4 | 5 | 95 | 0.5 |

Acidic Program "10 Min"

| Time (min) | A (%) | B (%) | Flow (mL/min) |
|---|---|---|---|
| 0 | 99 | 1 | 0.4 |
| 0.8 | 99 | 1 | 0.4 |
| 5.3 | 5 | 95 | 0.4 |
| 5.35 | 5 | 95 | 0.5 |
| 7.30 | 5 | 95 | 0.5 |

Crude materials could be purified by normal phase chromatography, (acidic or basic) reverse phase chromatography, chiral separation or recrystallization.

Normal reverse phase chromatography are performed using silica gel columns (100:200 mesh silica gel or Puriflash®-50SIHC-JP columns from Interchim).

Preparative Reverse Phase Chromatography are Performed as Follows:

LCMS purification (Basic mode, LCMS prep) using a SQD or QM Waters triple quadrupole mass spectrometer is used for LCMS purification. This spectrometer is equipped with an ESI source and a Prep LC controller Waters quaternary pump with diode array detector (210 to 400 nm).

MS Parameters:

ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC Parameters:

The reverse phase separation is carried out at rt on a XBridge prep OBD C18 column (5 µm, 30×50 mm) (basic elution). Gradient elution is done with Water (solvent A), ACN (solvent B), Ammonium bicarbonate in water 8 g/L+ 500 µL/L NH$_4$OH 30% (solvent C) (pH-8.5). HPLC flow rate: 35 mL/min to 60 mL/min, injection volume: 1 mL. The splitting ratio is set at +/−1/6000 to MS.

| Time (min) | A (%) | B (%) | C (%) | Flow (mL/min) |
|---|---|---|---|---|
| 0 | 85 | 5 | 10 | 35 |
| 1 | 85 | 5 | 10 | 35 |
| 7 | 5 | 85 | 10 | 35 |
| 9 | 5 | 95 | 0 | 60 |
| 12 | 5 | 95 | 0 | 60 |
| 12.5 | 85 | 5 | 10 | 35 |
| 16 | 85 | 5 | 10 | 35 |

Preparative Chiral Chromatographic separations are performed on using liquid phase chromatography or supercritical fluid chromatography (SFC) instruments with various mixtures of lower alcohols and $C_5$ to $C_8$ linear, branched or cyclic alkanes at 360 mL/min. Solvent mixtures as well as columns are described in individual procedures.

Products were generally dried under vacuum before final analyses and submission to biological testing.

NMR spectra are recorded on a BRUKER AVANCEIII 400 MHz-Ultrashield NMR Spectrometer fitted with a Windows 7 Professional workstation running Topspin 3.2 software and a 5 mm Double Resonance Broadband Probe (PABBI 1H/19F-BB Z-GRD Z82021/0075) or a 1 mm Triple Resonance Probe (PATXI 1H/D-13C/15N Z-GRD Z868301/004). The compounds were studied in DMSO-$d_6$, or CDCl$_3$ solution at a probe temperature of 300 K and at a concentration of 10 mg/mL. The instrument is locked on the deuterium signal of DMSO-$d_6$, or CDCl$_3$. Chemical shifts are given in ppm downfield from TMS (tetramethylsilane) taken as internal standard.

Optical rotations ([α]$_D$) were measured on a PERKIN-ELMER polarimeter 341 in a cuvette (I=1 dm) at a 10 mg/mL concentration, at a temperature mentioned in the specific examples, at 589 nm (sodium lamp).

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Example 1. Synthesis of (+)-3-[[2-(methoxymethyl)-6-(trifluoromethyl)imidazo[2,1-b][1,3,4]thiadiazol-5-yl]methyl]-5-propyl-oxazolidin-2-one 1 and (+3-[[2-(methoxymethyl)-6-(trifluoromethyl)imidazo[2,1-b][1,3,4]thiadiazol-5-yl]methyl]-5-propyl-oxazolidin-2-one 2 romethane over 12 CV) and the pure fractions were evaporated to dryness to give 1-nitropentan-2-ol 1 (4.7 g, 35.0 mmol) as a colorless oil.

Yield: 51%

$^1$H NMR (400 MHz, DMSO-d$_6$): δ 5.26 (d, J=6.2 Hz, 1H), 4.64 (dd, J=12.2, 3.2 Hz, 1H), 4.31 (dd, J=12.1, 9.3 Hz, 1H), 4.09 (ddt, J=8.9, 5.9, 3.2 Hz, 1H), 1.47-1.23 (m, 4H), 0.95-0.77 (m, 3H).

1.2 Synthesis of 1-aminopentan-2-ol II

A solution of 1-nitropentan-2-ol I (1 eq., 200 mg, 1.5 mmol) in ethanol (8 mL) was hydrogenated on a 10% Pd/C cartridge, at 50° C., under H$_2$ pressure (50 bar) in a H-Cube reactor during 1 h (flow: 1 mL/min, 7.5 cycles). The crude mixture was evaporated to dryness and dried under high vacuum to give 1-aminopentan-2-ol II (140 mg, 1.22 mmol,) as colorless oil. The obtained crude compound was used directly in the next step without any further purification.

Yield: 81%

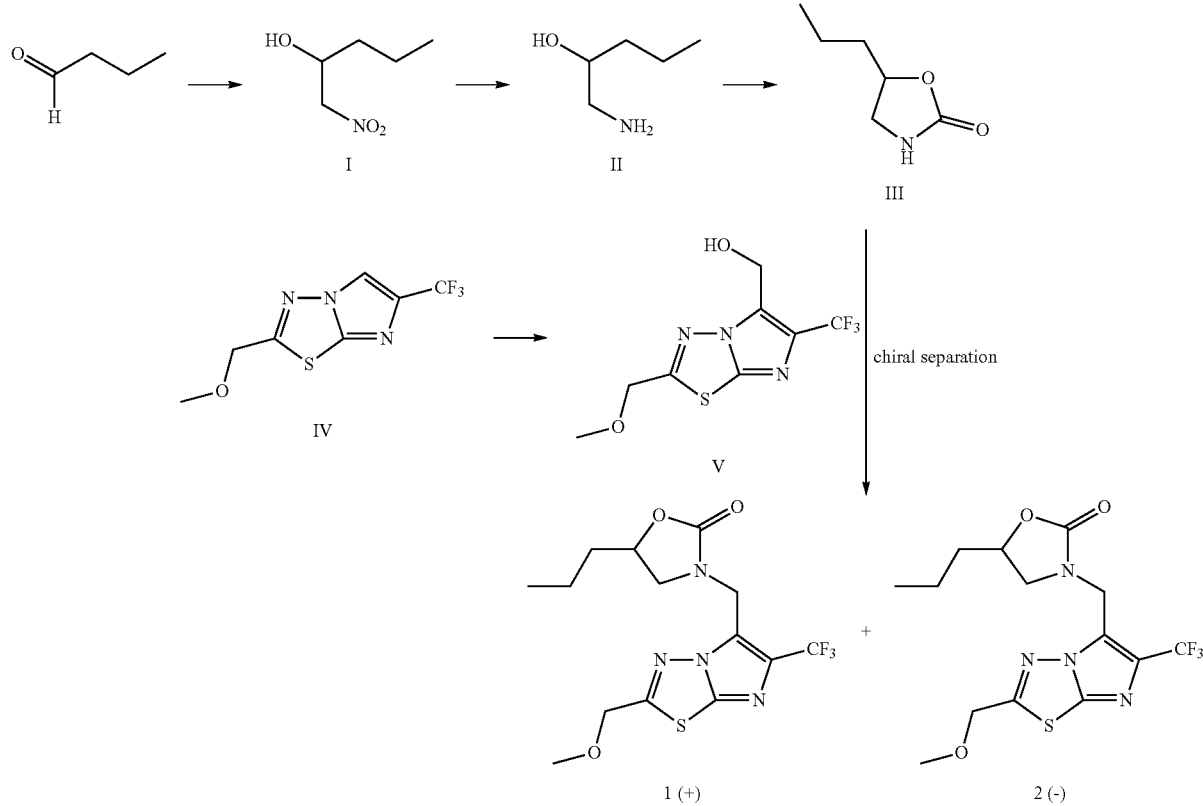

1.1 Synthesis of 1-nitropentan-2-ol I

A mixture of butyraldehyde (CAS: 123-72-8, 1 eq., 5.0 g, 69.3 mmol) and potassium carbonate (1 eq., 9.68 g, 69.3 mmol) in nitromethane (95 mL) was stirred at 50° C. for 5 h. The mixture was cooled to room temperature and ethyl acetate was added (100 mL). The organic layer was washed with water (two times), dried over MgSO$_4$, filtered and evaporated to dryness to give a brown oil. The crude mixture was purified by flash chromatography Biotage Isolera Four (100 g KP-SNAP silica gel column with 100% dichlo- $^1$H NMR (400 MHz, DMSO-d$_6$) δ 3.37-3.25 (m, 1H), 2.52 (d, J=4.1 Hz, 1H), 2.37 (dd, J=12.6, 7.3 Hz, 1H), 1.45-1.20 (m, 4H), 0.93-0.79 (m, 3H).

1.3 Synthesis of 5-propyloxazolidin-2-one III

To a solution of 1-aminopentan-2-ol II (1 eq., 1.0 g, 9.2 mmol) and 1,1'-carbonyldiimidazole (1 eq., 1.6 g, 9.7 mmol) in THF (20 mL) was added sodium hydride (0.1 eq., 23 mg, 0.92 mmol) and the mixture was stirred at 25° C. during 24 h. Ethyl acetate and water were added to the reaction mixture and the aqueous layer was extracted with ethyl acetate (two times), washed with water and brine, dried over MgSO$_4$, filtered and evaporated to dryness to give a yellow oil. The crude was purified by flash chromatography Biotage Isolera Four (50 g KP-SNAP silica gel column in a gradient of 0% to 10% methanol in dichloromethane over 10 CV) and the pure fractions were evaporated to dryness to give 5-propyloxazolidin-2-one III (990 mg, 7.59 mmol) as a white solid.

Yield: 82%

LC/MS: [M+H]$^+$=130.1

$^1$H NMR (400 MHz, CDCl$_3$): δ 5.98 (s, 1H), 4.73-4.55 (m, 1H), 3.65 (td, J=8.4, 0.8 Hz, 1H), 3.22 (ddd, J=8.2, 7.2, 0.9 Hz, 1H), 1.87-1.70 (m, 1H), 1.69-1.32 (m, 3H), 0.96 (t, J=7.3 Hz, 3H).

1.4 Synthesis of [2-(methoxymethyl)-6-(trifluoromethyl)imidazo[2,1-b][1,3,4]thiadiazol-5-yl]methanol V In a sealed tube, 2-(methoxymethyl)-6-(trifluoromethyl)imidazo[2,1-b][1,3,4]thiadiazole IV (CAS: 1294001-16-3, patent application WO 2012/143117, 1 eq., 2.0 g, 8.4 mmol), paraformaldehyde (6.0 eq., 1.52 g, 50.6 mmol) and an aqueous solution of hydrochloric acid (2N) (1.0 equiv., 4.2 mL, 8.4 mmol) were mixed in 1,4-dioxane (4 mL). The mixture was stirred at 100° C. for 18 h and the reaction was checked by LC/MS. The crude mixture was cooled to RT and an aqueous saturated solution of NaHCO$_3$ was added until pH=6-7. The aqueous layer was extracted with ethyl acetate (three times) and the combined organic layers were washed with brine, dried over MgSO$_4$, filtered and evaporated to dryness. The crude was purified by flash chromatography Biotage Isolera Four (100 g KP-SNAP silica gel column in a gradient of 0% to 10% methanol in dichloromethane over 15 CV) to give [2-(methoxymethyl)-6-(trifluoromethyl)imidazo[2,1-b][1,3,4]thiadiazol-5-yl]methanol (1.06 g, 3.5 mmol) V as a beige solid. The compound was used directly in the next step without any further purification.

Yield: 41%

LC/MS: [M+H]+=268.2

$^1$H NMR (400 MHz, CDCl$_3$): δ 5.04 (d, J=5.2 Hz, 2H), 4.77 (s, 2H), 3.53 (s, 3H), 2.32 (t, J=6.3 Hz, 1H).

1.5 Synthesis of (+)-3-[[2-(methoxymethyl)-6-(trifluoromethyl)imidazo[2,1-b][1,3,4]thiadiazol-5-yl]methyl]-5-propyl-oxazolidin-2-one 1 and (−)-3-[[2-(methoxymethyl)-6-(trifluoromethyl)imidazo[2,1-b][1,3,4]thiadiazol-5-yl]methyl]-5-propyl-oxazolidin-2-one 2

To a mixture of [2-(methoxymethyl)-6-(trifluoromethyl)imidazo[2,1-b][1,3,4]thiadiazol-5-yl]methanol V (1 eq., 200 mg, 0.74 mmol) and 5-propyloxazolidin-2-one III (2 eq., 190 mg, 1.48 mmol) in sulfolane (3 mL), was added p-toluenesulfonic acid monohydrate (1 eq., 152 mg, 0.74 mmol) and the mixture was stirred at 110° C. for 16 h. The crude mixture was directly purified by reverse phase preparative HPLC (basic conditions) to give a beige solid (155 mg of the racemate) which was purified by chiral SFC (Phase WhelkO1 (R,R), 50×227 mm/CO$_2$/EtOH Co-solvent 20%/30° C./360 mL/min). The purest fractions were evaporated to dryness to give (+)-3-[[2-(methoxymethyl)-6-(trifluoromethyl)imidazo[2,1-b][1,3,4]thiadiazol-5-yl]methyl]-5-propyl-oxazolidin-2-one 1 (first eluted, 56 mg, 0.15 mmol) and (−)-3-[[2-(methoxymethyl)-6-(trifluoromethyl) imidazo[2,1-b][1,3,4]thiadiazol-5-yl]methyl]-5-propyl-oxazolidin-2-one 2 (second eluted, 56 mg, 0.15 mmol) as colorless oils.

Yields: 20%

LC/MS: [M+H]$^+$=379.4

$^1$H NMR (400 MHz, DMSO-d$_6$): δ 4.84 (s, 2H), 4.74 (qd, J=15.8, 1.2 Hz, 2H), 4.44 (dtd, J=8.3, 7.0, 5.4 Hz, 1H), 3.54 (t, J=8.3 Hz, 1H), 3.43 (s, 3H), 3.08 (dd, J=8.4, 6.9 Hz, 1H), 1.62-1.45 (m, 2H), 1.28 (dddd, J=16.1, 13.6, 8.4, 4.0 Hz, 1H), 0.85 (t, J=7.4 Hz, 3H).

Alpha-D (1, MeOH, 10 mg/mL, 26.5° C.)=+27.0

Alpha-D (2, MeOH, 10 mg/mL, 26.5° C.)=−26.2

Example 2. (+)-3-[[6-(difluoromethyl)-2-(methoxymethyl)imidazo[2,1-b][1,3,4]thiadiazol-5-yl]methyl]-5-propyl-oxazolidin-2-one 3 and (+3-[[6-(difluoromethyl)-2-(methoxymethyl)imidazo[2,1-b][1,3,4]thiadiazol-5-yl]methyl]-5-propyl-oxazolidin-2-one 4

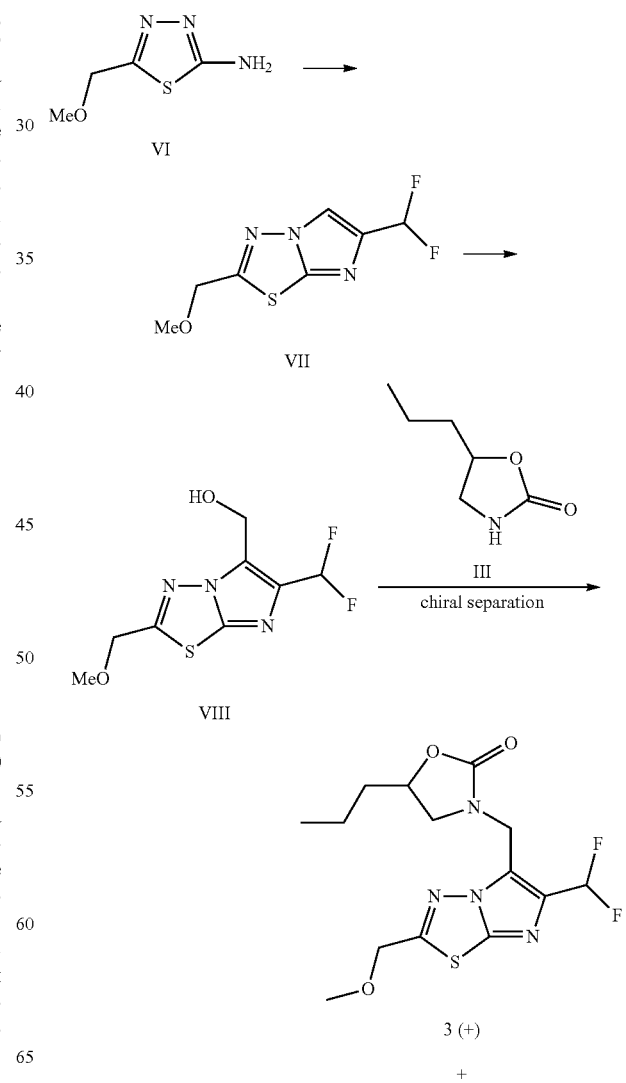

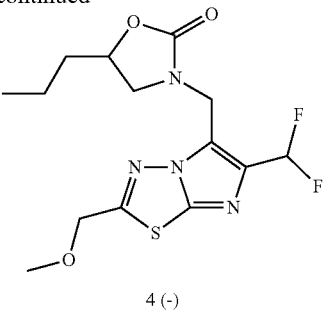

4 (−)

1.5 Synthesis of 6-(difluoromethyl)-2-(methoxymethyl)imidazo[2,1b][1,3,4]thiadiazole VII To a solution of 5-(methoxymethyl)-1,3,4-thiadiazol-2-amine VI (CAS: 15884-86-3, 1.0 eq., 6.5 g, 45 mmol) in DMF (100 mL), at 100° C., was added dropwise a solution of 3-bromo-1,1-difluoro-propan-2-one (CAS: 883233-85-0, 1.05 eq., 8.1 g, 47 mmol) in DMF (5 mL). The reaction mixture was heated at 100° C. during 3 h and the completion was checked by LC/MS. A saturated aqueous solution of NaHCO$_3$ was added and the organic layer was extracted with ethyl acetate (three times). The combined organic layers were washed with water (five times), dried over MgSO$_4$, filtered and evaporated to dryness to give a brown solid (7.6 g). The crude was purified by flash chromatography Biotage Isolera Four (100 g KP-SNAP silica gel column in a gradient of 0% to 5% methanol in dichloromethane over 12 CV) and the pure fractions were evaporated under high vacuum to give 6-(difluoromethyl)-2-(methoxymethyl)imidazo[2,1-b][1,3,4]thiadiazole VII (3.95 g, 17.8 mmol) as an orange solid.

Yield: 40%
LC/MS: [M+H]+=220.2
$^1$H NMR (400 MHz, DMSO-d$_6$): δ 8.53 (t, J=2.2 Hz, 1H), 7.01 (t, J=54.6 Hz, 1H), 4.83 (s, 2H), 3.43 (s, 3H).

1.6 Synthesis of [6-(difluoromethyl)-2-(methoxymethyl)imidazo[2,1-b][1,3,4]thiadiazol-5-yl]methanol VIII In a sealed tube, 6-(difluoromethyl)-2-(methoxymethyl)imidazo[2,1-b][1,3,4]thiadiazole VII (1.0 eq., 3.95 g, 18.0 mmol), paraformaldehyde (6.0 eq., 3.24 g, 108 mmol) and an aqueous solution of hydrochloric acid (2N) (0.9 equiv., 8.1 mL, 16.2 mmol) were mixed in 1,4-dioxane (8 mL). The mixture was stirred at 100° C. for 3.5 h and the reaction was checked by LC/MS. The crude mixture was cooled to RT and an aqueous saturated solution of NaHCO$_3$ was added until pH=6-7. The aqueous layer was extracted with ethyl acetate (three times) and the combined organic layers were washed with brine, dried over MgSO$_4$, filtered and evaporated to dryness. The crude was purified by flash chromatography Biotage Isolera Four (100 g KP-SNAP silica gel column in a gradient of 0% to 10% methanol in dichloromethane over 15 CV) to give a yellow oil (3 g) which was purified a second time by reverse phase HPLC (KROMASIL-Eternity XT C$_{18}$ 10 μm/ACN/H$_2$O/NH$_4$OH gradient from 20/80/0.1 to 50/50/0.1). The purest fractions were evaporated to dryness to give [6-(difluoromethyl)-2-(methoxymethyl)imidazo[2,1-b][1,3,4]thiadiazol-5-yl]methanol VIII (2 g, 8.02 mmol) as a white solid.

Yield: 45%
LC/MS: [M+H]+=250.2
$^1$H NMR (400 MHz, DMSO-d$_6$): δ 7.11 (t, J=53.6 Hz, 1H), 5.47 (t, J=5.4 Hz, 1H), 4.84 (s, 2H), 4.79 (d, J=5.5, Hz, 2H), 3.44 (d, J=0.9 Hz, 3H).

1.7. Synthesis of (+)-3-[[6-(difluoromethyl)-2-(methoxymethyl)imidazo[2,1-b][1,3,4]thiadiazol-5-yl]methyl]-5-propyl-oxazolidin-2-one 3 and (−)-3-[[6-(difluoromethyl)-2-(methoxymethyl)imidazo[2,1-b][1,3,4]thiadiazol-5-yl]methyl]-5-propyl-oxazolidin-2-one 4

To a mixture of [6-(difluoromethyl)-2-(methoxymethyl)imidazo[2,1-b][1,3,4]thiadiazol-5-yl]methanol VIII (1 eq., 200 mg, 0.8 mmol) and 5-propyloxazolidin-2-one III (2 eq., 206 mg, 1.6 mmol) in sulfolane (3 mL), was added p-toluenesulfonic acid monohydrate (1 eq., 152 mg, 0.8 mmol) and the mixture was stirred at 110° C. for 3.5 h. The crude mixture was directly purified by reverse phase preparative HPLC (basic conditions) to give a beige solid (216 mg of the racemate) which was purified by chiral SFC (Phase WhelkO1 (R,R), 50×227 mm/CO$_2$/EtOH Co-solvent 20%/30° C./360 mL/min). The purest fractions were evaporated to dryness to give (+)-3-[[6-(difluoromethyl)-2-(methoxymethyl)imidazo[2,1-b][1,3,4]thiadiazol-5-yl]methyl]-5-propyl-oxazolidin-2-one 3 (first eluted, 54 mg, 0.15 mmol, 19% yield) and (−)-3-[[6-(difluoromethyl)-2-(methoxymethyl)imidazo[2,1-b][1,3,4]thiadiazol-5-yl]methyl]-5-propyl-oxazolidin-2-one 4 (second eluted, 52 mg, 0.14 mmol, 18% Yield) as colorless oils.

Yields: 19% (3) and 18% (4)
LC/MS: [M+H]+=361.4
$^1$H NMR (400 MHz, DMSO-d$_6$): δ 7.12 (t, J=53.5 Hz, 1H), 4.83 (d, J=0.9 Hz, 2H), 4.81-4.66 (m, 2H), 4.46 (dtd, J=8.4, 7.0, 5.5 Hz, 1H), 3.56 (t, J=8.4 Hz, 1H), 3.44 (s, 3H), 3.09 (dd, J=8.4, 7.0 Hz, 1H), 1.65-1.42 (m, 2H), 1.39-1.17 (m, 2H), 0.86 (t, J=7.3 Hz, 3H).

Alpha-D (3, MeOH, 10 mg/mL, 27.7° C.)=+17.2

Example 3. Synthesis of (+)-3-[[2-[dideuterio(methoxy)methyl]-6-(trifluoromethyl)imidazo[2,1-b][1,3,4]thiadiazol-5-yl]methyl]-5-propyl-oxazolidin-2-one 5 and (−)-3-[[2-[dideuterio(methoxy)methyl]-6-(trifluoromethyl)imidazo[2,1-b][1,3,4]thiadiazol-5-yl]methyl]-5-propyl-oxazolidin-2-one 6

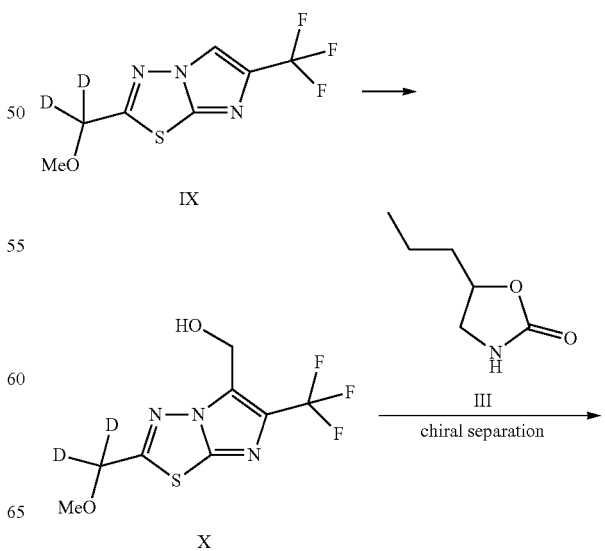

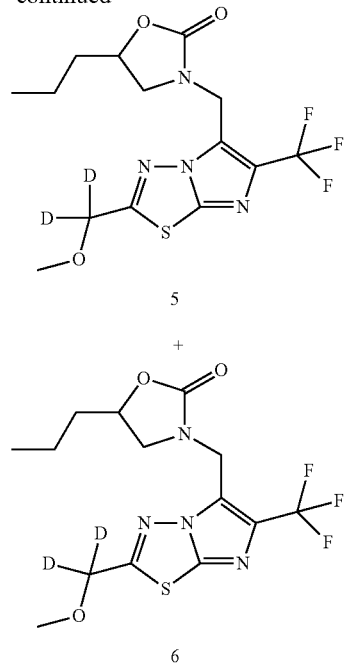

3.1 Synthesis of [2-[dideuterio(methoxy)methyl]-6-(trifluoromethyl)imidazo[2,1-b][1,3,4]thiadiazol-5-yl]methanol X A solution of 2-[dideuterio(methoxy)methyl]-6-(trifluoromethyl)imidazo[2,1-b][1,3,4]thiadiazole IX (WO2011047860, 1.0 eq., 1.25 g, 5.24 mmol), paraformaldehyde (6.0 equiv., 943 mg, 31.45 mmol) and hydrochloric acid (1.0 eq., 2.6 mL, 5.24 mmol) in 1,4-dioxane (2.6 mL) was stirred at 100° C. during 18 h. A saturated aqueous solution of $NaHCO_3$ was added and the aqueous layer was extracted with ethyl acetate (3 times). The combined organic layers were washed with brine, dried over $MgSO_4$, filtered and evaporated to dryness to give a yellow oil. The obtained crude was purified by flash chromatography Biotage Isolera Four (50 g KP-SNAP silica gel column from 100% dichloromethane to 10% methanol in dichloromethane over 15CV) to give a brown solid which was purified via reverse phase chromatography in basic mode. The purest fraction were evaporated to dryness to give [2-[dideuterio(methoxy)methyl]-6-(trifluoromethyl)imidazo[2,1-b][1,3,4]thiadiazol-5-yl]methanol X (475 mg, 1.73 mmol) as a white solid.

Yield: 33%
LC/MS: [M+H]$^+$=270.01
$^1$H NMR (400 MHz, DMSO-d6): δ 5.56 (s, 1H), 4.77 (s, 2H), 3.44 (s, 3H).

3.2 Synthesis of (+)-3-[[2-[dideuterio(methoxy)methyl]-6-(trifluoromethyl)imidazo[2,1-b][1,3,4]thiadiazol-5-yl]methyl]-5-propyl-oxazolidin-2-one 5 and (−)-3-[[2-[dideuterio(methoxy)methyl]-6-(trifluoromethyl)imidazo[2,1-b][1,3,4]thiadiazol-5-yl]methyl]-5-propyl-oxazolidin-2-one 6

To a mixture of [2-[dideuterio(methoxy)methyl]-6-(trifluoromethyl)imidazo[2,1-b][1,3,4]thiadiazol-5-yl]methanol X (1.0 eq., 200 mg, 0.74 mmol) and 5-propyloxazolidin-2-one III (2.0 eq., 190 mg, 1.47 mmol) in sulfolane (0.2 M, 3.5 mL), was added p-toluenesulfonic acid monohydrate (1.0 eq., 140 mg, 0.73 mmol) and the mixture was stirred at 110° C. for 16 h. The crude was directly purified by reverse phase chromatography in basic conditions to give of a yellow oil (172 mg). The mixture of enantiomers was purified via chiral SFC (W (3 μm)*EtOH 50%-heptane 50%-DEA 0.1%) to give (+)-3-[[2-[dideuterio(methoxy)methyl]-6-(trifluoromethyl)imidazo[2,1-b][1,3,4]thiadiazol-5-yl]methyl]-5-propyl-oxazolidin-2-one 5 (75 mg, 0.20 mmol) and (−)-3-[[2-[dideuterio(methoxy)methyl]-6-(trifluoromethyl)imidazo[2,1-b][1,3,4]thiadiazol-5-yl]methyl]-5-propyl-oxazolidin-2-one 6 (72 mg, 0.19 mmol) as colorless oils.

Global yield: 52% (26.5%+25.5%)
LC/MS: [M+H]$^+$=381.11
$^1$H NMR (400 MHz, CDCl$_3$): δ 5.00-4.75 (m, 2H), 4.51-4.40 (m, 1H), 3.51 (s, 4H), 3.04 (dd, J=8.4, 7.4 Hz, 1H), 1.76-1.66 (m, 1H), 1.60-1.50 (m, 1H), 1.48-1.29 (m, 2H), 0.92 (t, J=7.3 Hz, 3H).

Alpha-D (5, MeOH, 10 mg/mL, 25° C.)=+17.6

Example 4. Synthesis of (+)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one 7 and (−)-3-[[2-[deuterio(trideuteriomethoxy)methyl]-6-(trifluoromethyl)imidazo[2,1-b][1,3,4]thiadiazol-5-yl]methyl]-5-propyl-oxazolidin-2-one 8

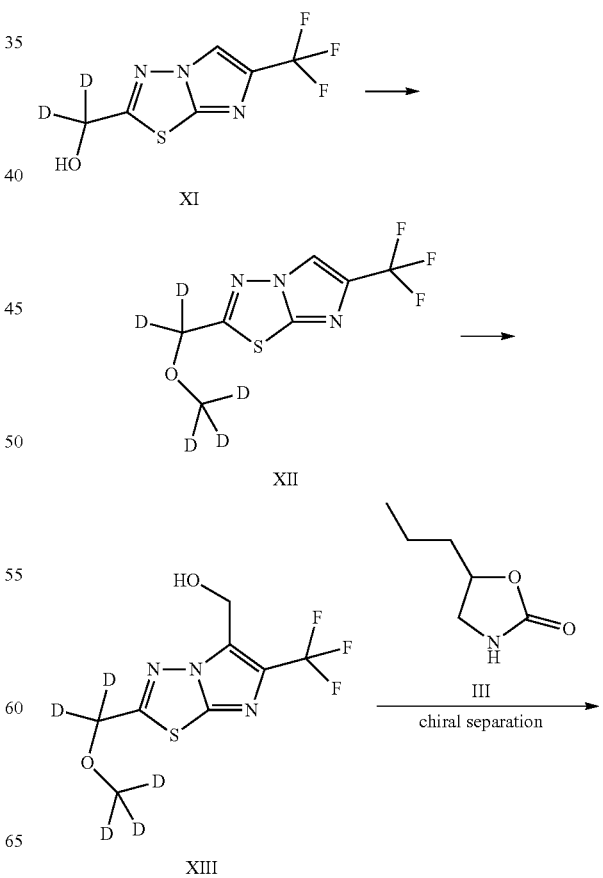

-continued

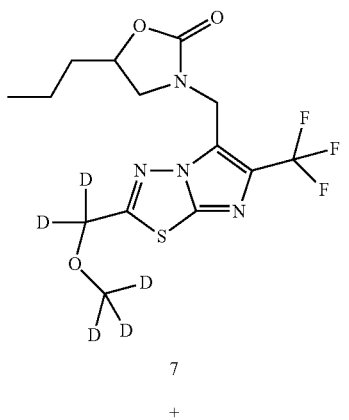

7

+

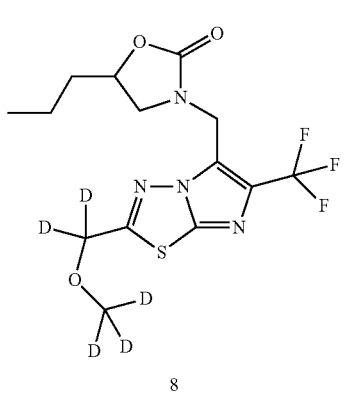

8

4.1 Synthesis of -[dideuterio(trideuteriomethoxy)methyl]-6-(trifluoromethyl)imidazo[2,1-b][1,3,4]thiadiazole XII To a solution of dideuterio-[6-(trifluoromethyl)imidazo[2,1-b][1,3,4]thiadiazol-2-yl]methanol XI (WO2011047860, 1.0 eq., 3.25 g, 13.0 mmol) in methanol (100 mL), at room temperature, was added silver oxide (1.3 eq., 3.9 g, 16.9 mmol) and iodomethane-d3 (4.0 eq., 3.23 mL, 52.0 mmol). The reaction mixture was stirred at 40° C. during 20 h. The mixture was then filtered through a pad of Celite and evaporated to dryness. A saturated aqueous solution of NaHCO₃ was added and the aqueous layer was extracted with ethyl acetate (3 times). The combined organic layers were dried over MgSO₄, filtered and evaporated to dryness to give a yellow oil which was purified by flash chromatograpy Biotage Isolera Four (100 g KP-SNAP silica gel column from 100% dichloromethane to 5% methanol in dichloromethane over 15CV) to give 2-[dideuterio(trideuteriomethoxy)methyl]-6-(trifluoromethyl)imidazo[2,1-b][1,3,4]thiadiazole XII (2.11 g, 7.4 mmol) as a white solid.

Yield: 57%

LC/MS: [M+H]+=243.08

$^1$H NMR (400 MHz, DMSO-d6): δ 8.90 (s, 1H).

4.2 Synthesis of [2-[dideuterio(trideuteriomethoxy)methyl]-6-(trifluoromethyl)imidazo[2,1-b][1,3,4]thiadiazol-5-yl]methanol XIII A solution of 2-[dideuterio(trideuteriomethoxy)methyl]-6-(trifluoromethyl)imidazo[2,1-b][1,3,4]thiadiazole XII (1.0 eq., 1.0 g, 4.1 mmol), paraformaldehyde (6.0 eq., 743 mg, 24.7 mmol) and hydrochloric acid (1.0 eq., 4.1 mmol, 2.0 mL) in 1,4-dioxane (2 mL) was stirred at 100° C. during 18 h. A saturated aqueous solution of NaHCO₃ was added and the aqueous layer was extracted with ethyl acetate (3 times). The combined organic layers were washed with brine, dried over MgSO₄, filtered and evaporated to dryness to give a yellow oil which was purified via reverse phase chromatography in basic mode. The purest fraction were evaporated to dryness to give [2-[dideuterio(trideuteriomethoxy)methyl]-6-(trifluoromethyl)imidazo[2,1-b][1,3,4]thiadiazol-5-yl]methanol XIII (560 mg, 1.97 mmol) as a white solid.

Yield: 48%

LC/MS: [M+H]+=270.01

$^1$H NMR (400 MHz, DMSO-d6): δ 5.30-6.30 (br s, 1H) 4.77 (d, J=1.3 Hz, 2H).

4.3 Synthesis of (+)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one 7 and (−)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one 8

To a mixture of [2-[dideuterio(trideuteriomethoxy)methyl]-6-(trifluoromethyl)imidazo[2,1-b][1,3,4]thiadiazol-5-yl]methanol XIII (1.0 eq., 200 mg, 0.73 mmol) and 5-propyloxazolidin-2-one III (2.0 eq., 190 mg, 1.47 mmol) in sulfolane (0.2 M, 3.5 mL), was added p-toluenesulfonic acid monohydrate (1.0 eq., 101 mg, 0.53 mmol) and the mixture was stirred at 110° C. for 16 h. The crude was purified by reverse phase chromatography in basic conditions to give of a yellow oil (175 mg). The mixture of enantiomers was purified by chiral SFC (W (3 μm)*EtOH 50%-heptane 50%-DEA 0.1%) to give (+)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one 7 (47 mg, 0.12 mmol) and (−)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one 8 (51 mg, 0.13 mmol) as clear oils.

Global Yield: 35% (17%+18%)

LC/MS: [M+H]+=384.14

$^1$H NMR (400 MHz, CDCl₃): δ 4.95 (dd, J=15.7, 1.2 Hz, 1H), 4.79 (dd, J=15.6, 1.2 Hz, 1H), 4.47 (qd, J=7.7, 5.2 Hz, 1H), 3.49 (t, J=8.4 Hz, 1H), 3.13-2.95 (m, 1H), 1.70 (dddd, J=12.8, 9.6, 7.5, 5.2 Hz, 1H), 1.57-1.49 (m, 1H), 1.48-1.28 (m, 2H), 0.93 (t, J=7.3 Hz, 3H).

Alpha-D (7, MeOH, 10 mg/mL, 25° C.)=+26.9

Example 5. Synthesis of give (+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 9 and (−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 10 using a H-cube reactor equipped with a Raney Ni cartridge (flow 1 mL/min, 50° C., 50 bar). The mixture was evaporated to dryness to give 1-amino-4,4,4-trifluoro-butan-2-ol XV (2.5 g, 17 mmol) as a colorless oil.

Yield: 63%

$^1$H NMR (400 MHz, CDCl$_3$): δ 3.89 (tt, J=8.0, 3.9 Hz, 1H), 2.86 (dd, J=12.8, 3.5 Hz, 1H), 2.62 (dd, J=12.8, 8.3 Hz, 1H), 2.35-2.07 (m, 2H).

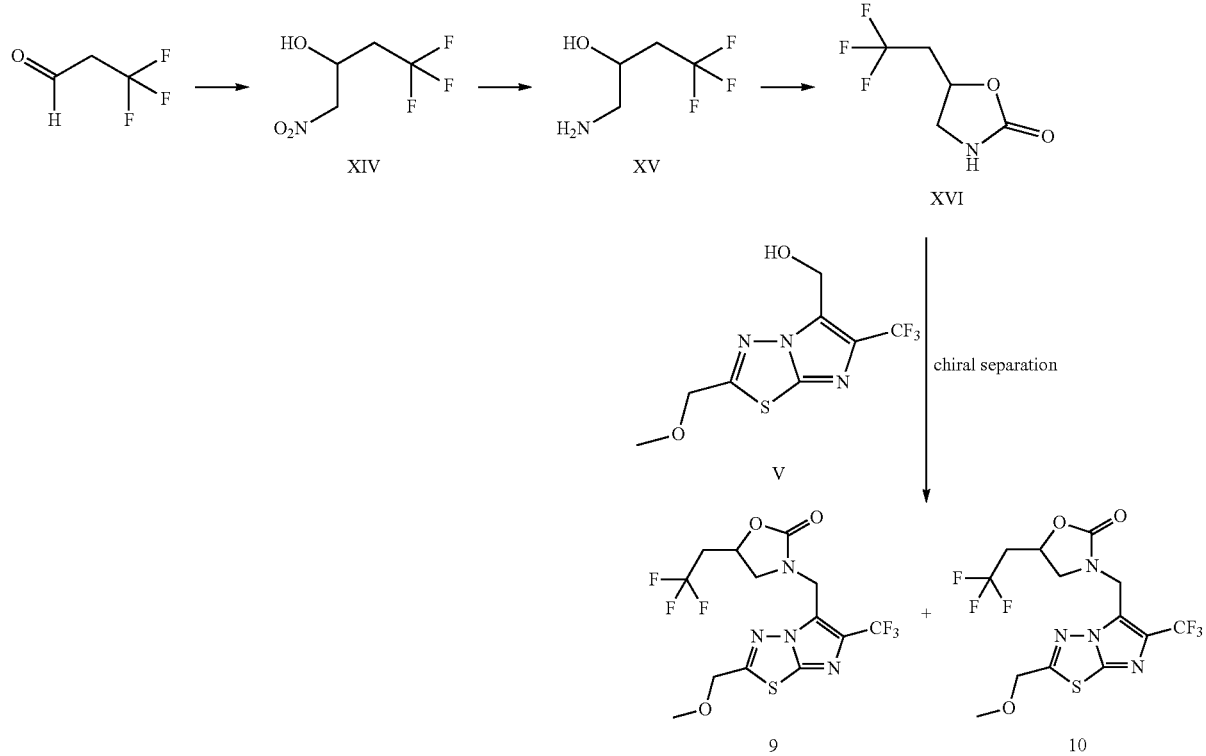

5.1 Synthesis of 4,4,4-trifluoro-1-nitro-butan-2-ol XIV

A mixture of 3,3,3-trifluoropropanal (1.0 eq., 5.0 g, 44.62 mmol), potassium carbonate (1.0 eq., 6.2 g, 44 mmol) and nitromethane (30 eq., 60.2 mL, 1340 mmol) was stirred at 50° C. for 5 h. The mixture was cooled to room temperature and diluted with water and ethyl acetate. The aqueous layer was extracted with ethyl acetate (3 times) and the combined organic layers were washed with water (2 times), dried over MgSO$_4$, filtered and evaporated to dryness. The crude was purified by flash chromatography Biotage Isolera Four (100 g KP-SNAP silica gel column gradient: 100% dichloromethane over 10 CV). The purest fractions were evaporated to dryness to give 4,4,4-trifluoro-1-nitro-butan-2-ol XIV (3.8 g, 22 mmol) as a colorless oil.

Yield: 49%

$^1$H NMR (400 MHz, CDCl$_3$): δ 4.73 (dddd, J=12.7, 7.6, 5.0, 3.8 Hz, 1H), 4.58-4.43 (m, 2H), 3.01 (d, J=5.1 Hz, 1H), 2.60-2.28 (m, 2H).

5.2 Synthesis of 1-amino-4,4,4-trifluoro-butan-2-ol XV

A mixture of 4,4,4-trifluoro-1-nitro-butan-2-ol XIV (1.0 eq., 4.8 g, 28 mmol) in ethanol (140 mL) was hydrogenated

5.3 Synthesis of 5-(2,2,2-trifluoroethyl)oxazolidin-2-one XVI

To a mixture of 1-amino-4,4,4-trifluoro-butan-2-ol XV (1.0 eq., 2.5 g, 17 mmol) and 1,1'-carbonyldiimidazole (1.0 eq., 2.9 g, 18 mmol) in THF (35 mL) was added sodium hydride (0.1 eq., 42 mg, 1.75 mmol) and the mixture was stirred at 25° C. for 16 h. A few drops of water were added (NaH neutralization) and the mixture was directly evaporated to dryness and purified by reverse phase chromatography in basic mode to give 5-(2,2,2-trifluoroethyl)oxazolidin-2-one XVI (2.25 g, 13.2 mmol) as a white solid Yield: 75%

LC/MS: [M+H]$^+$=170.11

$^1$H NMR (400 MHz, DMSO-d6): δ 7.61 (s, 1H), 4.81 (qd, J=7.6, 4.9 Hz, 1H), 3.62 (t, J=8.7 Hz, 1H), 3.20 (dd, J=8.9, 7.2 Hz, 1H), 2.89-2.68 (m, 2H).

5.4 Synthesis of (+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 9 and (−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 10

To a mixture of [2-(methoxymethyl)-6-(trifluoromethyl)imidazo[2,1-b][1,3,4]thiadiazol-5-yl]methanol V (1.0 eq., 200 mg, 0.75 mmol) and 5-(2,2,2-trifluoroethyl)oxazolidin-2-one XVI (1.8 eq., 227 mg, 1.34 mmol) in sulfolane (0.5 M, 3.7 mL), was added p-toluenesulfonic acid monohydrate (1.0 eq., 142 mg, 0.75 mmol) and the mixture was stirred at 110° C. for 3 h 30. The mixture was directly purified via reverse phase chromatography in basic conditions to give a yellow oil (250 mg). The obtained mixture of enantiomers was purified by chiral preparative HPLC (AS*EtOH 50%-heptane 50%-DEA 0.1%) to give (+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 9 (29 mg, 0.07 mmol) and (−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 10 (30 mg, 0.07 mmol).

Global yield: 19% (9.3%+9.6%)
LC/MS: [M+H]$^+$=419.05
$^1$H NMR (400 MHz, CDCl$_3$): δ 5.02-4.66 (m, 5H), 3.66 (t, J=8.7 Hz, 1H), 3.52 (s, 3H), 3.33-3.17 (m, 1H), 2.76-2.58 (m, 1H), 2.51-2.35 (m, 1H).
Alpha-D (9, MeOH, 10 mg/mL, 25° C.)=+13.0

(+)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one 11 and (−)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one 12 are synthesized according to the same procedure starting from 5-(2,2,2-trifluoroethyl)oxazolidin-2-one XVI and [6-(difluoromethyl)-2-(methoxymethyl)imidazo[2,1-b][1,3,4]thiadiazol-5-yl]methanol VIII.

Global yield: 14% (7.8%+6.2%)
LC/MS: [M+H]$^+$=401.06

$^1$H NMR (400 MHz, DMSO-d6): δ 7.14 (t, J=53.5 Hz, 1H), 4.90-4.60 (m, 5H), 3.67 (t, J=8.6 Hz, 1H), 3.43 (s, 3H), 3.25 (dd, J=8.6, 7.0 Hz, 1H), 2.91-2.63 (m, 2H).
Alpha-D (11, MeOH, 10 mg/mL, 25° C.)=+3.6

Example 6. Synthesis of give (−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 13 and (+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one 14

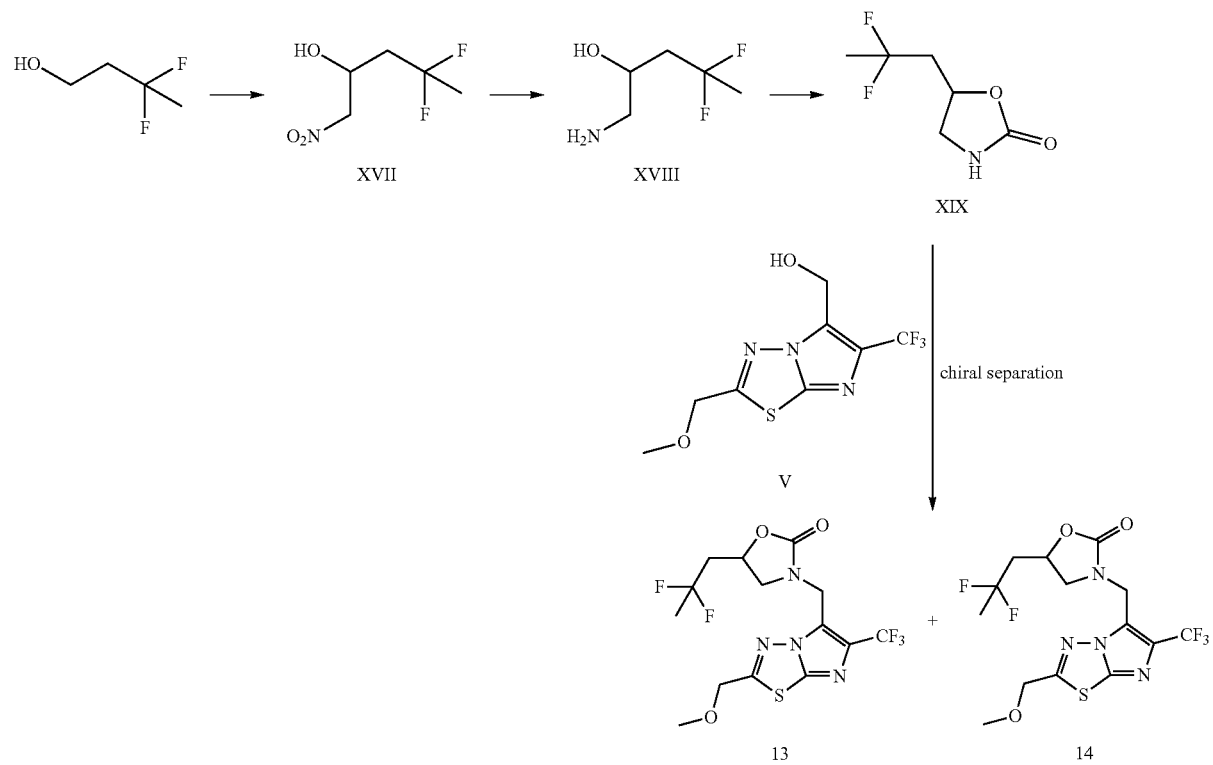

6.1 Synthesis of 4,4-difluoro-1-nitro-pentan-2-ol XVII

To a solution of 3,3-difluorobutan-1-ol (1.0 eq., 1.5 g, 9.8 mmol) in dichloromethane (50 mL) at 0° C. was added Dess-Martin periodinane (1.2 eq., 5.1 g, 12 mmol) and the reaction mixture was stirred at 0° C. during 2 h. The crude mixture was then cooled to −78° C., filtered and the obtained solid was washed with cold dichloromethane (−78° C.). To the obtained filtrate warmed at room temperature was added potassium carbonate (15.0 eq., 21 g, 150 mmol) and nitromethane (30.0 eq., 18 g, 290 mmol) and the mixture was stirred at 45° C. during 2 h. The crude mixture was filtered on Celite and the obtained filtrate was concentrated under vacuum at 30° C. to give a yellow gum. The obtained gum was purified by flash chromatography Biotage Isolera Four (100 g KP-SNAP silica gel column in a gradient 100% dichloromethane over 6CV than 0% to 10% methanol in dichloromethane over 10CV) to give 4,4-difluoro-1-nitro-pentan-2-ol XVII (678 mg, 4.0 mmol) as a yellow oil.

Yield: 41%

¹H NMR (400 MHz, CDCl₃): δ 4.71 (tt, J=7.9, 4.0 Hz, 1H), 4.61-4.36 (m, 2H), 2.79 (dd, J=4.6, 1.7 Hz, 1H), 2.32-2.03 (m, 2H), 1.71 (t, J=18.9 Hz, 3H).

6.2 Synthesis of 1-amino-4,4-difluoro-pentan-2-ol XVIII

A solution of 4,4-difluoro-1-nitro-pentan-2-ol XVII (1.0 eq., 1 g, 5.91 mmol) in ethanol (40 mL) was hydrogenated in a H-Cube equipped with a 10%/Pd cartridge (flow 1 mL/min, 50° C., 50 bar).The crude mixture was evaporated to dryness to give 1-amino-4,4-difluoro-pentan-2-ol XVIII (760 mg, 4.9 mmol) as a colorless oil.

Yield: 83%

¹H NMR (400 MHz, CDCl₃): δ 3.95-3.76 (m, 1H), 2.88 (dd, J=12.7, 3.6 Hz, 1H), 2.58 (dd, J=12.7, 8.2 Hz, 1H), 2.16-1.88 (m, 2H), 1.69 (t, J=18.9 Hz, 3H).

6.3 Synthesis of 5-(2,2-difluoropropyl)oxazolidin-2-one XIX

To a solution of 1-amino-4,4-difluoro-pentan-2-ol XVIII (1.0 eq., 760 mg, 5.46 mmol) in THF (18 mL) at room temperature were added 1,1'-carbonyldiimidazole (1.0 eq., 876 mg, 5.30 mmol) and sodium hydride (0.1 eq., 21 mg, 0.53 mmol). The reaction was stirred at room temperature during 16 h. A few drops of water were added to the solution (NaH neutralization) and the mixture was evaporated to dryness. The crude was directly purified by flash chromatography Biotage Isolera Four (100 g KP-SNAP silica gel column in a gradient of 0% to 10% methanol in dichloromethane over 10CV, than 10% of Methanol over 4CV) to give 5-(2,2-difluoropropyl)oxazolidin-2-one XIX (675 mg, 4.08 mmol) as a beige solid.

Yield: 75%

¹H NMR (400 MHz, CDCl₃): δ 5.34 (d, J=37.0 Hz, 1H), 4.96-4.85 (m, 1H), 3.78 (td, J=8.5, 8.0, 0.9 Hz, 1H), 3.37 (t, J=8.2 Hz, 1H), 2.56-2.18 (m, 2H), 1.71 (t, J=18.9 Hz, 3H).

6.4 Synthesis of (+5-(2,2-difluoropropyl)-3-[[2-(methoxymethyl)-6-(trifluoromethyl)imidazo[2,1-b][1,3,4]thiadiazol-5-yl]methyl]oxazolidin-2-one 13 and (+)-5-(2,2-difluoropropyl)-3-[[2-(methoxymethyl)-6-(trifluoromethyl)imidazo[2,1-b][1,3,4]thiadiazol-5-yl]methyl]oxazolidin-2-one 14

To a mixture of [2-(methoxymethyl)-6-(trifluoromethyl)imidazo[2,1-b][1,3,4]thiadiazol-5-yl]methanol V (1.0 eq., 150 mg, 0.56 mmol) and 5-(2,2-difluoropropyl)oxazolidin-2-one XIX (1.5 eq., 139 mg, 0.84 mmol) in sulfolane (3 mL), was added p-toluenesulfonic acid monohydrate (1.0 eq., 106 mg, 0.56 mmol). The mixture was stirred for 16 h at 100° C. The mixture was directly purified by reverse phase chromatography in basic mode to give a yellow oil. The mixture of enantiomers was purified by chiral SFC (AS*EtOH 50%-heptane 50%-DEA 0.1%) to give (+5-(2,2-difluoropropyl)-3-[[2-(methoxymethyl)-6-(trifluoromethyl)imidazo[2,1-b][1,3,4]thiadiazol-5-yl]methyl]oxazolidin-2-one 13 (19.1 mg, 0.05 mmol) and (+)-5-(2,2-difluoropropyl)-3-[[2-(methoxymethyl)-6-(trifluoromethyl)imidazo[2,1-b][1,3,4]thiadiazol-5-yl]methyl]oxazolidin-2-one 14 (19.9 mg, 0.05 mmol) as white solids.

Global yield: 16.7% (8.2%+8.5%)

LC/MS: [M+H]⁺=415.02

¹H NMR (400 MHz, DMSO-d₆): δ 4.90-4.55 (m, 5H), 3.63 (t, J=8.4 Hz, 1H), 3.45 (s, 3H), 3.22 (t, J=8.0 Hz, 1H), 2.42-2.26 (m, 2H), 1.63 (t, J=19.3 Hz, 3H).

Alpha-D (13, MeOH, 10 mg/mL, 28.6° C.)=−13.3

3-[[6-(difluoromethyl)-2-(methoxymethyl)imidazo[2,1-b][1,3,4]thiadiazol-5-yl]methyl]-5-(2,2-difluoropropyl)oxazolidin-2-one 15 and 3-[[6-(difluoromethyl)-2-(methoxymethyl)imidazo[2,1-b][1,3,4]thiadiazol-5-yl]methyl]-5-(2,2-difluoropropyl)oxazolidin-2-one 16 are synthesized according to the same procedure starting from 5-(2,2-difluoropropyl)oxazolidin-2-one XIX and [6-(difluoromethyl)-2-(methoxymethyl)imidazo[2,1-b][1,3,4]thiadiazol-5-yl]methanol VIII.

Global yield: 8% (4%+4%)

LC/MS: [M+H]⁺=397.04

¹H NMR (400 MHz, DMSO-d6): δ 7.13 (t, J=53.5 Hz, 1H), 4.89-4.60 (m, 5H), 3.64 (t, J=8.5 Hz, 1H), 3.43 (s, 3H), 3.21 (t, J=8.0 Hz, 1H), 2.41-2.17 (m, 2H), 1.62 (t, J=19.3 Hz, 3H).

Chiral chromatography (SFC, phase W, CO₂-MeOH 15%, 3 ml/min): peak 1 (15): 6.64 min and peak 2 (16): 7.72 min.

Table (I) indicates the IUPAC name (or the name generated from Accelerys Draw 4.0) of the compound, the ion peak observed in mass spectroscopy and the ¹H NMR description.

TABLE I

Physical Characterization of Example Compounds.

| n° | Compound NAME | Structure | MH⁺ | ¹H NMR δ (DMSO-d₆) |
|---|---|---|---|---|
| 1 | (+)-3-[[2-(methoxymethyl)-6-(trifluoromethyl)imidazo[2,1-b][1,3,4]thiadiazol-5-yl]methyl]-5-propyl-oxazolidin-2-one | 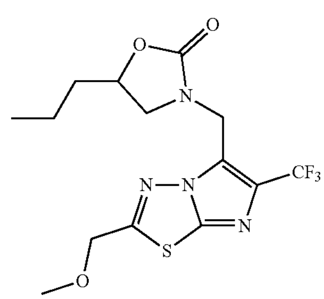 [SMILES: CCCC1CN(Cc2c(C(F)(F)F)nc3sc(COC)nn23)C(=O)O1] | 379.4 | 4.84 (s, 2H), 4.74 (qd, J = 15.8, 1.2 Hz, 2H), 4.44 (dtd, J = 8.3, 7.0, 5.4 Hz, 1H), 3.54 (t, J = 8.3 Hz, 1H), 3.43 (s, 3H), 3.08 (dd, J = 8.4, 6.9 Hz, 1H), 1.62-1.45 (m, 2H), 1.28 (dddd, J = 16.1, 13.6, 8.4, 4.0 Hz, 1H), 0.85 (t, J = 7.4 Hz, 3H). |

TABLE I-continued

Physical Characterization of Example Compounds.

| n° | Compound NAME | Structure | MH+ | $^1$H NMR δ (DMSO-$d_6$) |
|---|---|---|---|---|
| 2 | (−)-3-[[2-(methoxymethyl)-6-(trifluoromethyl)imidazo[2,1-b][1,3,4]thiadiazol-5-yl]methyl]-5-propyl-oxazolidin-2-one | 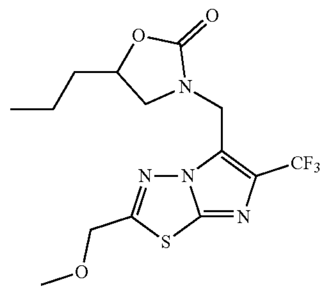 [SMILES: CCCC1CN(Cc2c(C(F)(F)F)nc3sc(COC)nn23)C(=O)O1] | 379.4 | 4.84 (s, 2H), 4.74 (qd, J = 15.8, 1.2 Hz, 2H), 4.44 (dtd, J = 8.3, 7.0, 5.4 Hz, 1H), 3.54 (t, J = 8.3 Hz, 1H), 3.43 (s, 3H), 3.08 (dd, J = 8.4, 6.9 Hz, 1H), 1.62-1.45 (m, 2H), 1.28 (dddd, J = 16.1, 13.6, 8.4, 4.0 Hz, 1H), 0.85 (t, J = 7.4 Hz, 3H). |
| 3 | (+)-3-[[6-(difluoromethyl)-2-(methoxymethyl)imidazo[2,1-b][1,3,4]thiadiazol-5-yl]methyl]-5-propyl-oxazolidin-2-one | 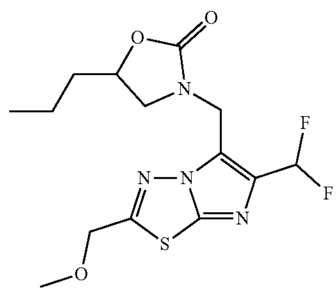 [SMILES: CCCC1CN(Cc2c(C(F)F)nc3sc(COC)nn23)C(=O)O1] | 361.4 | 5.00-4.75 (m, 2H), 4.51-4.40 (m, 1H), 3.51 (s, 4H), 3.04 (dd, J = 8.4, 7.4 Hz, 1H), 1.76-1.66 (m, 1H), 1.60-1.50 (m, 1H), 1.48-1.29 (m, 2H), 0.92 (t, J = 7.3 Hz, 3H). |
| 4 | (−)-3-[[6-(difluoromethyl)-2-(methoxymethyl)imidazo[2,1-b][1,3,4]thiadiazol-5-yl]methyl]-5-propyl-oxazolidin-2-one | 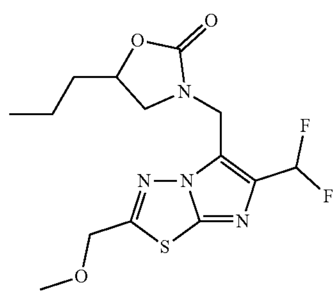 [SMILES: CCCC1CN(Cc2c(C(F)F)nc3sc(COC)nn23)C(=O)O1] | 361.4 | 5.00-4.75 (m, 2H), 4.51-4.40 (m, 1H), 3.51 (s, 4H), 3.04 (dd, J = 8.4, 7.4 Hz, 1H), 1.76-1.66 (m, 1H), 1.60-1.50 (m, 1H), 1.48-1.29 (m, 2H), 0.92 (t, J = 7.3 Hz, 3H). |
| 5 | (+)-3-[[2-[dideuterio(methoxy)methyl]-6-(trifluoromethyl)imidazo[2,1-b][1,3,4]thiadiazol-5-yl]methyl]-5-propyl-oxazolidin-2-one | 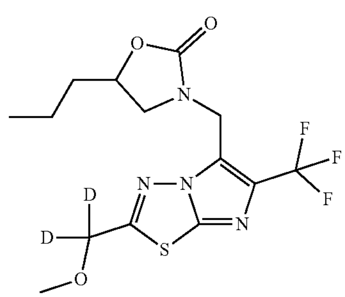 [SMILES: [2H]C([2H])(OC)c1nn2c(CN3CC(CCC)OC3=O)c(C(F)(F)F)nc2s1] | 381.1 | 5.00-4.75 (m, 2H), 4.51-4.40 (m, 1H), 3.51 (s, 4H), 3.04 (dd, J = 8.4, 7.4 Hz, 1H), 1.76-1.66 (m, 1H), 1.60-1.50 (m, 1H), 1.48-1.29 (m, 2H), 0.92 (t, J = 7.3 Hz, 3H). |
| 6 | (−)-3-[[2-[dideuterio(methoxy)methyl]-6-(trifluoromethyl)imidazo[2,1-b][1,3,4]thiadiazol-5-yl]methyl]-5-propyl-oxazolidin-2-one | 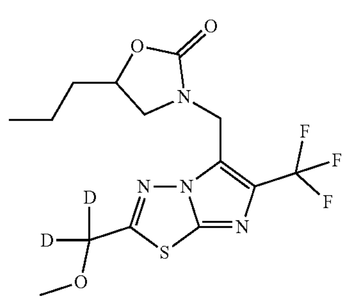 [SMILES: [2H]C([2H])(OC)c1nn2c(CN3CC(CCC)OC3=O)c(C(F)(F)F)nc2s1] | 381.1 | 5.00-4.75 (m, 2H), 4.51-4.40 (m, 1H), 3.51 (s, 4H), 3.04 (dd, J = 8.4, 7.4 Hz, 1H), 1.76-1.66 (m, 1H), 1.60-1.50 (m, 1H), 1.48-1.29 (m, 2H), 0.92 (t, J = 7.3 Hz, 3H). |

TABLE I-continued

Physical Characterization of Example Compounds.

| n° | Compound NAME | Structure | MH+ | ¹H NMR δ (DMSO-d$_6$) |
|---|---|---|---|---|
| 7 | (+)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one | 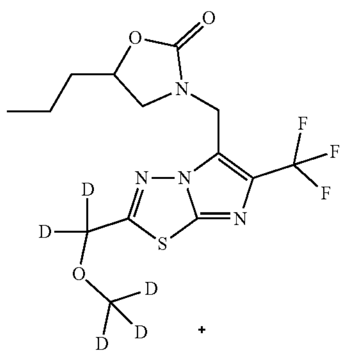 [SMILES: [2H]C([2H])([2H])OC([2H])([2H])c1nn2c(CN3CC(CCC)OC3=O)c(C(F)(F)F)nc2s1] | 384.1 | 4.95 (dd, J = 15.7, 1.2 Hz, 1H), 4.79 (dd, J = 15.6, 1.2 Hz, 1H), 4.47 (qd, J = 7.7, 5.2 Hz, 1H), 3.49 (t, J = 8.4 Hz, 1H), 3.13-2.95 (m, 1H), 1.70 (dddd, J = 12.8, 9.6, 7.5, 5.2 Hz, 1H), 1.57-1.49 (m, 1H), 1.48-1.28 (m, 2H), 0.93 (t, J = 7.3 Hz, 3H). |
| 8 | (−)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one | 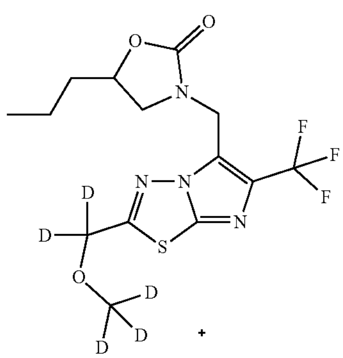 [SMILES: [2H]C([2H])([2H])OC([2H])([2H])c1nn2c(CN3CC(CCC)OC3=O)c(C(F)(F)F)nc2s1] | 384.1 | 4.95 (dd, J = 15.7, 1.2 Hz, 1H), 4.79 (dd, J = 15.6, 1.2 Hz, 1H), 4.47 (qd, J = 7.7, 5.2 Hz, 1H), 3.49 (t, J = 8.4 Hz, 1H), 3.13-2.95 (m, 1H), 1.70 (dddd, J = 12.8, 9.6, 7.5, 5.2 Hz, 1H), 1.57-1.49 (m, 1H), 1.48-1.28 (m, 2H), 0.93 (t, J = 7.3 Hz, 3H). |
| 9 | (+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one | 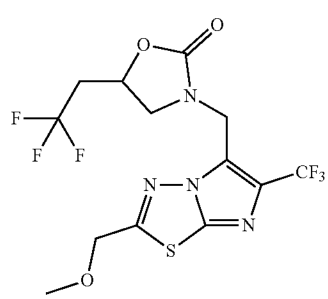 [SMILES: COCc1nn2c(CN3CC(CC(F)(F)F)OC3=O)c(C(F)(F)F)nc2s1] | 419.0 | 5.02-4.66 (m, 5H), 3.66 (t, J = 8.7 Hz, 1H), 3.52 (s, 3H), 3.33-3.17 (m, 1H), 2.76-2.58 (m, 1H), 2.51-2.35 (m, 1H). |
| 10 | (−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one | 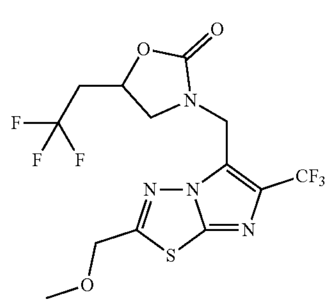 [SMILES: COCc1nn2c(CN3CC(CC(F)(F)F)OC3=O)c(C(F)(F)F)nc2s1] | 419.0 | 5.02-4.66 (m, 5H), 3.66 (t, J = 8.7 Hz, 1H), 3.52 (s, 3H), 3.33-3.17 (m, 1H), 2.76-2.58 (m, 1H), 2.51-2.35 (m, 1H). |

TABLE I-continued

Physical Characterization of Example Compounds.

| n° | Compound NAME | Structure | MH+ | $^1$H NMR δ (DMSO-$d_6$) |
|---|---|---|---|---|
| 11 | (+)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one | 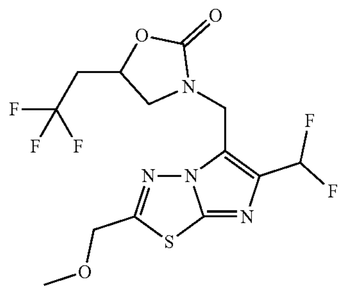 [SMILES: COCc1nn2c(CN3CC(CC(F)(F)F)OC3=O)c(C(F)F)nc2s1] | 401.0 | 7.14 (t, J = 53.5 Hz, 1H), 4.90-4.60 (m, 5H), 3.67 (t, J = 8.6 Hz, 1H), 3.43 (s, 3H), 3.25 (dd, J = 8.6, 7.0 Hz, 1H), 2.91-2.63 (m, 2H). |
| 12 | (−)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one | 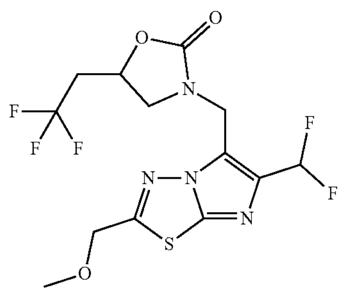 [SMILES: COCc1nn2c(CN3CC(CC(F)(F)F)OC3=O)c(C(F)F)nc2s1] | 401.0 | 7.14 (t, J = 53.5 Hz, 1H), 4.90-4.60 (m, 5H), 3.67 (t, J = 8.6 Hz, 1H), 3.43 (s, 3H), 3.25 (dd, J = 8.6, 7.0 Hz, 1H), 2.91-2.63 (m, 2H). |
| 13 | (−)-5-(2,2-difluoropropyl)-3-[[2-(methoxymethyl)-6-(trifluoromethyl)imidazo[2,1-b][1,3,4]thiadiazol-5-yl]methyl]oxazolidin-2-one | 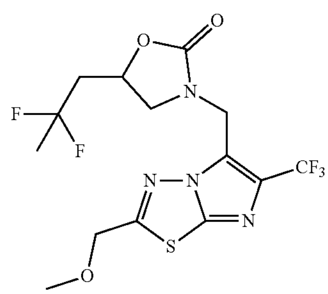 [SMILES: COCc1nn2c(CN3CC(CC(C)(F)F)OC3=O)c(C(F)(F)F)nc2s1] | 415.0 | 4.90-4.55 (m, 5H), 3.63 (t, J = 8.4 Hz, 1H), 3.45 (s, 3H), 3.22 (t, J = 8.0 Hz, 1H), 2.42-2.26 (m, 2H), 1.63 (t, J = 19.3 Hz, 3H). |
| 14 | (+)-5-(2,2-difluoropropyl)-3-[[2-(methoxymethyl)-6-(trifluoromethyl)imidazo[2,1-b][1,3,4]thiadiazol-5-yl]methyl]oxazolidin-2-one | 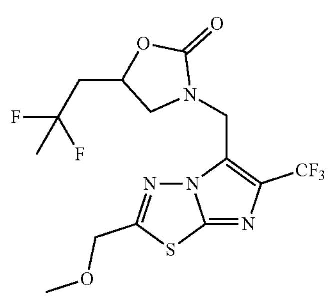 [SMILES: COCc1nn2c(CN3CC(CC(C)(F)F)OC3=O)c(C(F)(F)F)nc2s1] | 415.0 | 4.90-4.55 (m, 5H), 3.63 (t, J = 8.4 Hz, 1H), 3.45 (s, 3H), 3.22 (t, J = 8.0 Hz, 1H), 2.42-2.26 (m, 2H), 1.63 (t, J = 19.3 Hz, 3H). |
| 15 | 3-[[6-(difluoromethyl)-2-(methoxymethyl)imidazo[2,1-b][1,3,4]thiadiazol-5-yl]methyl]-5-(2,2-difluoropropyl)oxazolidin-2-one (enantiomer 1) | 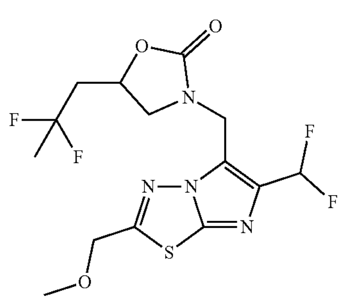 [SMILES: COCc1nn2c(CN3CC(CC(C)(F)F)OC3=O)c(C(F)F)nc2s1] | 397.0 | 7.13 (t, J = 53.5 Hz, 1H), 4.89-4.60 (m, 5H), 3.64 (t, J = 8.5 Hz, 1H), 3.43 (s, 3H), 3.21 (t, J = 8.0 Hz, 1H), 2.41-2.17 (m, 2H), 1.62 (t, J = 19.3 Hz, 3H). |

TABLE I-continued

Physical Characterization of Example Compounds.

| n° | Compound NAME | Structure | MH+ | ¹H NMR δ (DMSO-d$_6$) |
|---|---|---|---|---|
| 16 | 3-[[6-(difluoromethyl)-2-(methoxymethyl)imidazo[2,1-b][1,3,4]thiadiazol-5-yl]methyl]-5-(2,2-difluoropropyl)oxazolidin-2-one (enantiomer 2) | 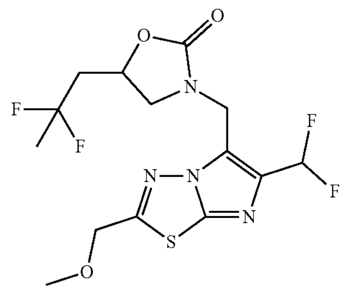 [SMILES: COCc1nn2c(CN3CC(CC(C)(F)F)OC3=O)c(C(F)F)nc2s1] | 397.0 | 7.13 (t, J = 53.5 Hz, 1H), 4.89-4.60 (m, 5H), 3.64 (t, J = 8.5 Hz, 1H), 3.43 (s, 3H), 3.21 (t, J = 8.0 Hz, 1H), 2.41-2.17 (m, 2H), 1.62 (t, J = 19.3 Hz, 3H). |

Example 7. Binding Assays to SV2A and SV2C

Human SV2A and SV2C proteins were expressed in human embryonic kidney (HEK) cells. HEK SV2A and HEK SV2C membrane preparations were prepared as described in Gillard et al (Eur. J. Pharmacol. 2006, 536, 102-108). To measure affinity of non-labelled compounds, competition experiments were performed as follow: Membranes expressing SV2 proteins (5 to 15 µg proteins per assay) were incubated for 60 min at 37° C. with either [³H]-2-[4-(3-azidophenyl)-2-oxo-1-pyrrolidinyl]butanamide (5 nM) and/or [³H]-4R-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one (25 nM) in 0.2 ml of a 50 mM Tris-HCl buffer (pH 7.4) containing 2 mM MgCl$_2$, 0.1% dimethylsulfoxide and ten increasing concentrations of non-labelled test compound (0.1 nM to 10 µM). At the end of the incubation period, the membrane-bound radioligand was recovered by rapid filtration through GF/C glass fiber filters pre-soaked in 0.1% polyethyleneimine. Membranes were washed with at least 4 times the assay volume of ice-cold 50 mM Tris HCl buffer (pH 7.4). The filters were dried and the radioactivity determined by liquid scintillation. The entire filtration step did not exceed 10 sec. Measured affinity pIC$_{50}$ values were corrected to pKi according to Cheng and Prusoff (Biochem. Pharmacol. 1973, 22(23), 3099-3108).

Compounds of formula (I) according to the invention typically show pKi SV2A values of at least 6.5. and pKi SV2C values of at least 6.0.

Example 8. Seizure Models

Male NMRI mice (Charles River, Germany) weighing 22-32 g are used in all experiments. The animals are kept on a 12/12-h light/dark cycle with lights on at 6:00 am and are housed at a temperature maintained at 20-21° C. and at humidity of about 40%. The mice are housed in groups of 10 per cage (Type III). All animals have free access to standard pellet food and water before random assignment to experimental groups consisting of 10 mice each. All animal experiments are done according to the National Rules on Animal Experiments and conducted in accordance with the guidelines of the European Community Council directive 2010/63/EU. A local ethical committee approved the experimental protocols.

8.1 6 Hz Seizure Model

The 6 Hz model is carried out according to a previously described protocol (Kaminski et al., Epilepsia (2004), 45, 864-867). Briefly, corneal stimulation (44 mA, 0.2 ms-duration monopolar rectangular pulses at 6 Hz for 3 s) is delivered by a constant-current device (ECT Unit 57800; Ugo Basile, Comerio, Italy). A drop of 0.4% oxybuprocaine hydrochloride (Unicaine, Thea, France) is placed on the eyes before electrical stimulation. During the stimulation, mice are manually restrained and released into the observation cage (38×26×14 cm) immediately after the current application. The seizures are often preceded by a brief period (~2-3 s) of intense locomotor agitation (wild running and jumping). The animals then exhibit a "stunned" posture associated with rearing, forelimb automatic movements and clonus, twitching of the vibrissae, and Strub-tail. At the end of the seizure, animals resume their normal exploratory behavior. The experimental endpoint is protection against the seizure. The animal is considered to be protected if it resumes its normal exploratory behavior within 7 s from the stimulation.

In vivo activities determined for test compounds are typically comprised between 0.05 mg/kg and 20 mg/kg after single IP dosing.

8.2 Pentylenetetrazol (PTZ) Seizure Model

Pentylenetetrazol is used at the previously established CD97 dose of 89 mg/kg; a convulsive dose inducing clonic convulsions of all four extremities in 97% of mice (Klitgaard et al., Eur. J. Pharmacol. (1998), 353, 191-206). Immediately following pentylenetetrazol injection the mice are placed individually in Perspex cages and observed for the presence of clonic convulsions in all four extremities and tonic hindlimb extension during 60 min period.

In vivo activities determined for test compounds are typically comprised between 0.5 mg/kg and 30 mg/kg after single IP dosing.

Example 9. Azamulin Assay

Cryopreserved human hepatocytes (pool of 20 donors, BSU batch from Celsis/IVT/Bioreclamation) were thawed accordingly the provider's information. Viability (trypan blue exclusion) was higher than 75%. Pre-incubations (250 µL of hepatocytes suspension at 2×10⁶ hepatocytes/mL) were carried out with William's medium, containing 2 mM of glutamine and 15 mM of Hepes, in 48-well plates at +37° C., in an incubator (5% CO$_2$), under gentle agitation (vibrating agitator, Titramax 100, ca 300 rpm) during 30 min. After the pre-incubation, the incubation was initiated by adding to hepatocytes, 250 µL of culture medium (see composition above) containing UCB compound (1 µM) or midazolam (positive control) with or without azamulin (6 µM—specific CYP3A4/5 inhibitor). Final concentrations of UCB compound and azamulin in the incubates are 0.5 µM and 3 µM, respectively. The cell suspensions was rapidly re-homogenized by 2 in-out pipetting. After 0, 30, 60, 120, 180 and 240 minutes of incubation, reactions were stopped by transferring 50 µl of incubates into the appropriate well from 96-well plate containing 50 µL of ice cold acetonitrile with ketoconazole 1 µM as internal standard. Before each sampling, cell incubates are re-homogenized by 2 in out pipetting.

Once the incubation is finished, 96-well plates are centrifuged at ca 3700 rpm, +4° C., for 15 minutes. 50 µL of supernatants are transferred into the wells of other deep well plates to which 150 µL of H$_2$O Millipore were added. These samples were are analyzed by micro UPLC/HR-MS for parent disappearance and monitoring of metabolite formation.

The CYP3A4/5 contribution known as fraction metabolized by CYP3A4/5 ($f_{m,CYP3A4/5}$) was calculated for each compound from the ratio between CLint (based on parent parent drug disappearance) in absence and in presence of azamulin, by using the following equation:

$$Fm_{CYP3A4/5} = 1 - \frac{CL_{int\ with\ azamulin}}{CL_{int\ without\ azamulin}}$$

Fraction metabolized by CYP3A4/5 ($f_{m,CYP3A4/5}$) of test compounds are typically comprised between 0 and 40%.

The invention claimed is:

1. A compound having formula (I), or a geometrical isomer, enantiomer, diastereomer, isotope or mixture thereof, or a pharmaceutically acceptable salt thereof,

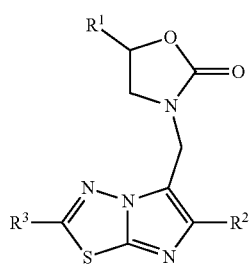

(I)

wherein
R$^1$ is a C$_{1-4}$ alkyl optionally substituted by one or more halogen substituents;
R$^2$ is a halogen atom, or a C$_{1-4}$ alkyl optionally substituted by one or more halogen atoms;
R$^3$ is a C$_{1-4}$ alkyl substituted by an alkoxy substituent.

2. A compound according to claim 1, wherein R$^1$ is an i-butyl, a n-propyl, a 2,2-difluoropropyl, a 2-chloro-2,2-difluoroethyl, a 2,2-difluoroethyl, a 2,2,2-trifluoroethyl or a 2-fluoroethyl moiety.

3. A compound according to claim 1, wherein R$^1$ is n-propyl, a 2,2-difluoropropyl, or a 2,2,2-trifluoroethyl moiety.

4. A compound according to claim 1, wherein R$^2$ is a chlorine atom, a difluoromethyl moiety, or a trifluoromethyl moiety.

5. A compound according to claim 1, wherein R$^2$ is a difluoromethyl moiety or a trifluoromethyl moiety.

6. A compound according to claim 1, wherein R$^3$ is a methoxymethyl, a [($^2$H$_3$)methyloxy]methyl, a methoxy ($^2$H$_2$)methyl, or a [($^2$H$_3$)methyloxy]($^2$H$_2$)methyl moiety.

7. A compound according to claim 1, wherein
R$^1$ is a n-propyl, a 2,2-difluoropropyl or a 2,2,2-trifluoroethyl moiety;
R$^2$ is a difluoromethyl or a trifluoromethyl moiety;
R$^3$ is a methoxymethyl, a [($^2$H$_3$)methoxy]methyl, a [($^2$H$_3$) methoxy] ($^2$H$_2$) methyl or a methoxy($^2$H$_2$) methyl moiety.

8. A compound according to claim 1 which is:
(+)-3-[[2-(methoxymethyl)-6-(trifluoromethyl)imidazo[2,1-b][1,3,4]thiadiazol-5-yl]methyl]-5-propyl-oxazolidin-2-one;
(−)-3-[[2-(methoxymethyl)-6-(trifluoromethyl)imidazo[2,1-b][1,3,4]thiadiazol-5-yl]methyl]-5-propyl-oxazolidin-2-one;
(+)-3-[[6-(difluoromethyl)-2-(methoxymethyl)imidazo[2,1-b][1,3,4]thiadiazol-5-yl]methyl]-5-propyl-oxazolidin-2-one;
(−)-3-[[6-(difluoromethyl)-2-(methoxymethyl)imidazo[2,1-b][1,3,4]thiadiazol-5-yl]methyl]-5-propyl-oxazolidin-2-one;
(+)-3-[[2-[dideuterio(methoxy)methyl]-6-(trifluoromethyl)imidazo[2,1-b][1,3,4]thiadiazol-5-yl]methyl]-5-propyl-oxazolidin-2-one;
(−)-3-[[2-[dideuterio(methoxy)methyl]-6-(trifluoromethyl)imidazo[2,1-b][1,3,4]thiadiazol-5-yl]methyl]-5-propyl-oxazolidin-2-one;
(+)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one;
(−)-3-[[2-[dideuterio(trideuteriomethoxy)methyl]-6-(trifluoromethyl)imidazo[2,1-b][1,3,4]thiadiazol-5-yl]methyl]-5-propyl-oxazolidin-2-one;
(+)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one;
(−)-3-[[2-(methoxymethyl)-6-(trifluoromethyl)imidazo[2,1-b][1,3,4]thiadiazol-5-yl]methyl]-5-(2,2,2-trifluoroethyl)oxazolidin-2-one;
(+)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one;
(−)-3-[[6-(difluoromethyl)-2-(methoxymethyl)imidazo[2,1-b][1,3,4]thiadiazol-5-yl]methyl]-5-(2,2,2-trifluoroethyl)oxazolidin-2-one;
(−)-5-(2,2-difluoropropyl)-3-[[2-(methoxymethyl)-6-(trifluoromethyl)imidazo[2,1-b][1,3,4]thiadiazol-5-yl]methyl]oxazolidin-2-one;
(+)-5-(2,2-difluoropropyl)-3-[[2-(methoxymethyl)-6-(trifluoromethyl)imidazo[2,1-b][1,3,4]thiadiazol-5-yl]methyl]oxazolidin-2-one;
3-[[6-(difluoromethyl)-2-(methoxymethyl)imidazo[2,1-b][1,3,4]thiadiazol-5-yl]methyl]-5-(2,2-difluoropropyl)oxazolidin-2-one, enantiomer 1;
3-[[6-(difluoromethyl)-2-(methoxymethyl)imidazo[2,1-b][1,3,4]thiadiazol-5-yl]methyl]-5-(2,2-difluoropropyl)oxazolidin-2-one, enantiomer 2.

9. A pharmaceutical composition comprising an effective amount of a compound according to claim 1 in combination with a pharmaceutically acceptable diluent or carrier.

10. A method for the treatment of epilepsy, epileptogenesis, seizure disorders, or convulsions, comprising administering to a patient in need thereof an effective amount of a compound or salt according to claim 1.

11. A method according to claim 9, wherein the treatment is for refractory seizures.

12. A compound according to claim 2, wherein $R^2$ is a chlorine atom, a difluoromethyl moiety, or a trifluoromethyl moiety.

13. A compound according to claim 3, wherein $R^2$ is a difluoromethyl moiety or a trifluoromethyl moiety.

14. A compound according to claim 2, wherein $R^3$ is a methoxymethyl, a [($^2$H$_3$)methyloxy]methyl, a methoxy($^2$H$_2$)methyl, or a [($^2$H$_3$)methyloxy]($^2$H$_2$)methyl moiety.

15. A compound according to claim 4, wherein $R^3$ is a methoxymethyl, a [($^2$H$_3$)methyloxy]methyl, a methoxy($^2$H$_2$)methyl, or a [($^2$H$_3$)methyloxy]($^2$H$_2$)methyl moiety.

* * * * *